(12) United States Patent
Chang et al.

(10) Patent No.: US 6,749,863 B1
(45) Date of Patent: Jun. 15, 2004

(54) TARGETED LIPOSOME GENE DELIVERY

(75) Inventors: Esther H. Chang, Chevy Chase, MD (US); Liang Xu, Arlington, VA (US); Kathleen Pirollo, Arlington, VA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/601,444

(22) PCT Filed: Nov. 19, 1998

(86) PCT No.: PCT/US98/24657

§ 371 (c)(1),
(2), (4) Date: Jan. 4, 2001

(87) PCT Pub. No.: WO99/25320

PCT Pub. Date: May 27, 1999

Related U.S. Application Data

(60) Provisional application No. 60/083,175, filed on Apr. 27, 1998, and provisional application No. 60/066,188, filed on Nov. 19, 1997.

(51) Int. Cl.$^7$ .......................... A61K 9/127; A61K 48/00
(52) U.S. Cl. ................... 424/450; 435/320.1; 435/455; 435/458; 514/44
(58) Field of Search .......................... 424/450; 514/44; 435/320.1, 455, 458

(56) References Cited

U.S. PATENT DOCUMENTS

| | | | |
|---|---|---|---|
| 5,635,380 A | | 6/1997 | Naftilan et al. |
| 5,783,566 A | * | 7/1998 | Mislick ......................... 514/44 |
| 5,851,818 A | * | 12/1998 | Huang et al. ............. 435/320.1 |
| 6,028,066 A | * | 2/2000 | Unger ......................... 514/180 |
| 6,030,956 A | * | 2/2000 | Boulikas ...................... 514/44 |
| 6,069,134 A | * | 5/2000 | Roth et al. .................... 514/44 |
| 6,071,533 A | | 6/2000 | Papahadjopoulos et al. |
| 6,077,834 A | * | 6/2000 | Cheng .......................... 514/44 |
| 6,303,378 B1 | * | 10/2001 | Bridenbaugh et al. ...... 435/455 |
| 6,414,139 B1 | * | 7/2002 | Unger et al. ................. 536/413 |

FOREIGN PATENT DOCUMENTS

| WO | WO 95/21259 A1 | 8/1995 |
|---|---|---|

OTHER PUBLICATIONS

Lee et al., Critial Reviews in Therapeutic Drug Carrier Systesm, 14, 2:173–206, 1997.*
Kao et al. (Cancer Gene Therapy, 3, 4:250–256, 1996).*
Verma et al. (Nature, vol. 389, 18:239–242, Sep. 1997).*
Anderson, Nature, vol. 392:25–30, 1998).*
Filion (International J. of Pharmaceutics, 162:159–170, 1996.*
Wang et al. (Biochemistry, vol. 92:3318–3312, 1995).*
Cheng (Human Gene Therapy, vol. 7: 275–282, 1996).*
Lee et al. (J. of Biological Chemistry, vol. 271, No. 14, pp. 8481–8487, 1996).*
Gao et al. (Biochemistry, 35: 1027–1036, 1996).*
Ledley, Human Gene Therapy, vol. 6:1129–1144, 1995.*
Nishikawa, Human Gene Therapy, vol. 12:861–870, 2001.*
Aoki, K et al. "Liposome–mediated in Vivo Gene Transfer of Antisense K–ras Construct Inhibits Pancreatic Tumor Dissemination in the Murine Peritoneal Cavity", *Cancer Research*, Sep. 1, 1995; 55:3810–3816.
Dzau, V.J. et al. "Fusigenic viral liposome for gene therapy in cardiovascular diseases", *Proc. Natl. Acad. Sci. USA*, Oct. 1996; 93:11421–11425.
Feero, W.G. et al. "Selection and use of ligands of receptor–mediated gene delivery to myogenic cells", *Gene Therapy*, 1997; 4:664–674.
Filion, M.C. et al. "Toxicity and immunomodulatory activity of liposomal vectors formulated with cationic lipids toward immune effector cells", *Biochimica et Biophysica Acta*, 1997; 1329:345–356.
Grimaldi, S. et al. "Attempts to use liposomes and RBC ghosts as vectors in drug and antisense therapy of virus infection", *Res. Virol.*, 1997; 148:177–180.
He, Y. et al. "Growth Inhibition of Human Papillomavirus 16 DNA–positive Mouse Tumor by Antisense RNA Transcribed from U6 Promoter", *Cancer Research*, Sep. 15, 1997; 57:3993–3999.
Lappalainen, K. et al. "Cationic liposomes mediated delivery of antisense oligonucleotides targeted to HPV 16 E7 mRNA in CaSki cells", *Antiviral Research*, 1994; 23:119–130.
Lavigne, C. et al. "Enhanced Antisense Inhibition of Human Immunodeficiency Virus Type 1 in Cell Cultures by DLS Delivery System", *Biochemical and Biophysical Research Communications*, 1997; 237:566–571.

(List continued on next page.)

*Primary Examiner*—Dave T. Nguyen
(74) *Attorney, Agent, or Firm*—Rothwell, Figg, Ernst & Manbeck

(57) ABSTRACT

Targeted ligand-liposome-therapeutic molecule complexes (vectors) for the systemic delivery of the therapeutic molecule to various target cell types including cancer cells such as squamous cell carcinoma of the head and neck, breast and prostate tumors. The preferred ligands, folate and transferrin, target the liposome complex and facilitate transient gene transfection. The systemic delivery of complexes containing DNA encoding wild-type p53 to established mouse xenografts markedly sensitized the tumors to radiotherapy and chemotherapy. The combination of systemic p53 gene therapy and conventional radiotherapy or chemotherapy resulted in total tumor regression and long tern inhibition of recurrence. This cell-specific delivery system was also used in vivo to successfully deliver, via intravenous administration, small DNA molecules (oligonucleotides) resulting in chemosensitivity and xenograft growth inhibition. Other therapeutic molecules, including intact viruses, can be encapsulated in a complex and targeted in accordance with the invention.

56 Claims, 1 Drawing Sheet

OTHER PUBLICATIONS

Lee, R.J. et al. "Folate–targeted, Anionic Liposome–entrapped Polylysine–condensed DNA for Tumor Cell–specific Gene Transfer", *The Journal of Biological Chemistry*, Apr. 5, 1996; 271(14):8481–8487.

Morishita, R. et al. "Molecular Delivery System for Antisense Oligonucleotides: Enhanced Effectiveness of Antisense Oligonucleotides by HVJ–liposome Mediated Transfer", *J. Cardiovasc. Pharmacol. Therapeut.*, 1996: 2(3):213–222.

Plank, C. et al. "Activation of the Complement System by Synthetic DNA Complexes: A Potential Barrier for Intravenous Gene Delivery", *Human Gene Therapy*; Aug. 1, 1996; 7:1437–1446.

Renneisen, K. et al. "Inhibition of Expression of Human Immunodeficiency Virus–1 in Vitro by Antibody–targeted Lipsomes Containing Antisense RNA to the env Region", *The Journal of Biological Chemistry*, Sep. 25, 1990; 265(27):16337–16342.

Ropert, C. et al. "Oligonu7cleotides Encapsulateed in pH Sensitive Liposomes are Efficient Toward Friend Retrovirus", *Biochemcial and Biophysical Research Communications*, Mar. 16, 1992; 183(2):879–885.

Seth, P. et al. "Adenovirus–mediated Gene Transfer to Human Breast Tumor Cells: An Approach for Cancer Gene Therapy and Bone Marrow Purging", *Cancer Research*, Mar. 15, 1996; 56:1346–1351.

Wagner, E. et al. "Influenza virus hemagglutinin HA–2 N–terminal fusogenic peptides augment gene transfer by transferrin–polylysine–DNA complexes: Toward a synthetic virus–like gene –transfer vehicle", *Proc. Natl. Acad. Sci. USA*, Sep. 1992; 89:7934–7938.

Xu, M. et al. "Parenteral Gene Therapy with p53 Inhibits Human Breast Tumors In Vivo Through a Bystander Mechanism Without Evidence of Toxicity", *Human Gene Therapy*, Jan. 20, 1997; 8:177–185.

Zelphati, O. et al. "Synthesis and anti–HIV activity of thiocholesteryl–coupled phosphodiester antisense oligonucleotides incorporated into immunolliposomes", *Antiviral Research*, 1994; 25:13–25.

Zelphati, O. et al. "Antisense oligonucleotides in solution or encapuslted in immunoliposomes inhibit replicationof HIV–1 by several different mechanisms", *Nucleic Acids Research*, 1994; 22(20):4307–4314.

* cited by examiner-

TARGETED LIPOSOME GENE DELIVERY

CROSS-REFERENCE TO RELATED APPLICATIONS

This application is related to provisional applications serial Nos. 60/066,188, filed Nov. 19, 1997, and 60/083,175, filed Apr. 27, 1998.

BACKGROUND OF THE INVENTION

1. Field of the Invention

This invention relates generally to the systemic delivery of a therapeutic molecule via a liposome complex that is targeted to a pre-selected cell type. More specifically, the invention provides compositions and methods for cell-targeted gene transfer and gene therapy for human cancers whereby a therapeutic molecule is delivered to the targeted cancer cell via a ligand/liposome complex. Treatment of cell proliferative disease (e.g. cancer) results in substantial improvement of the efficacy of radiation and chemotherapeutic interventions.

2. Description of Related Art

The ideal therapeutic for cancer would be one that selectively targets a cellular pathway responsible for the tumor phenotype and would be nontoxic to normal cells. To date, the ideal therapeutic remains just that—an ideal. While cancer treatments involving gene therapy and anti-sense molecules have substantial promise, there are many issues that need to be addressed before this promise can be realized. Perhaps foremost among the issues associated with macromolecular treatments for cancer and other diseases is the efficient delivery of the therapeutic molecule(s) to the site(s) in the body where they are needed.

A variety of nucleic acid delivery systems ("vectors") to treat cancer have been evaluated by others, including viruses and liposomes. The ideal vector for human cancer gene therapy would be one that could be systemically administered and then specifically and efficiently target tumor cells wherever they occur in the body. Viral vector-directed methods show high gene transfer efficiency but are deficient in several areas. The limitations of a viral approach are related to their lack of targeting and to the presence of residual viral elements that can be immunogenic, cytopathic, or recombinogenic.

A major deficiency of viral vectors is the lack of cancer cell specificity. Absent tumor targeting capability, viral vectors are limited in use to direct, local delivery that does not have the capability to reach metastatic disease—the ultimate cause of death for the majority of cancer patients.

The high titers achievable and the cell tropism that makes viruses attractive as gene therapy and gene transfer delivery vectors present some of their greatest deficiencies. Although the preparation of novel viruses with new targets for infection has been described in the literature, these vectors are problematic due to the need for growing virus to high titer. Consequently, a substantial amount of attention has been directed to non-viral vectors for the delivery of molecular therapeutics, including use in gene transfer and gene therapy.

Progress has been made toward developing non-viral, pharmaceutical formulations of genes for in vivo human therapy, particularly cationic liposome-mediated gene transfer systems. Cationic liposomes are composed of positively charged lipid bilayers and can be complexed to negatively charged, naked DNA by simple mixing of lipids and DNA such that the resulting complex has a net positive charge. The complex is easily bound and taken up by cells, with a relatively high transfection efficiency. Features of cationic liposomes that make them versatile and attractive for DNA delivery include: simplicity of preparation, the ability to complex large amounts of DNA, versatility in use with any type and size of DNA or RNA, the ability to transfect many different types of cells (including non-dividing cells) and lack of immunogenicity or biohazardous activity. The liposome approach offers a number of advantages over viral methodologies for gene delivery. Most significantly, since liposomes are not infectious agents capable of self-replication, they pose no risk of evolving into new classes of infectious human pathogens. Further, cationic liposomes have been shown to be safe and somewhat efficient for in vivo gene delivery. Since liposomes are not infectious agents, they can be formulated by simple mixing. Further, cationic liposomes have been shown to be safe and somewhat efficient for in vivo gene delivery. Clinical trials are now underway using cationic liposomes for gene delivery, and liposomes for delivery of small molecule therapeutics (e.g., chemotherapeutic and antifungal agents) are already on the market.

One disadvantage of cationic liposomes is that they lack tumor specificity and have relatively low transfection efficiencies as compared to viral vectors. However, targeting cancer cells via liposomes can be achieved by modifying the liposomes so that they bear a ligand recognized by a cell surface receptor. Receptor-mediated endocytosis represents a highly efficient internalization pathway in eukaryotic cells. The presence of a ligand on a liposome facilitates the entry of DNA into cells through initial binding of ligand by its receptor on the cell surface followed by internalization of the bound complex. Once internalized, sufficient DNA can escape the endocytic pathway to be expressed in the cell nucleus.

There now exists a substantial knowledge base regarding the molecules that reside on the exterior surfaces of cancer cells. Surface molecules can be used to selectively target liposomes to tumor cells, because the molecules that are found upon the exterior of tumor cells differ from those on normal cells. For example, if a liposome has the protein transferrin (Tf) on its surface, it can target cancer cells that have high levels of the transferrin receptor.

A variety of ligands have been examined for their liposome-targeting ability, including folic acid (folate), a vitamin necessary for DNA synthesis, and transferrin. Both the folate receptor and transferrin receptor levels are found to be elevated in various types of cancer cells including ovarian, oral, breast, prostate and colon. The presence of such receptors can correlate with the aggressive or proliferative status of tumor cells. The folate receptor has also been shown to recycle during the internalization of folate in rapidly dividing cells such as cancer cells. Moreover, the transferrin and folate-conjugated macromolecules and liposomes have been shown to be taken up specifically by receptor-bearing tumor cells by receptor mediated endocytosis. Thus the folate and transferrin receptors are considered to be useful as prognostic tumor markers for cancer and as potential targets for drug delivery in the therapy of malignant cell growth.

Failure to respond to radiotherapy and chemotherapy represents an unmet medical need in the treatment of many types of cancer. Often, when cancer recurs, the tumors have acquired increased resistance to radiation or to chemotherapeutic agents. The incorporation into cancer therapies of a new component which results in sensitization to these therapies would have immense clinical relevance. One way in which such chemo/radio sensitization could be achieved is via targeted gene therapy.

An important role for p53 in the control of cellular proliferation by the regulation of cell cycle events and induction of programmed cell death (apoptosis) has been established. Since it appears that most anti-cancer agents work by inducing apoptosis, inhibition of, or changes in, this pathway may lead to failure of therapeutic regimens. A direct link, therefore, has been suggested between abnormalities in p53 and resistance to cytotoxic cancer treatments (both chemo- and radiotherapy). It has also been suggested that the loss of p53 function may contribute to the cross-resistance to anti-cancer agents observed in some tumor cells. Various groups have established a positive correlation between the presence of mutant p53 and chemoresistance in mouse fibrosarcomas and in primary tumor cultures from breast carcinomas, human gastric and esophageal carcinomas, as well as B-cell chronic lymphoblastic leukemia. In addition, chemosensitivity via apoptosis reportedly was restored by expression of wtp53 in non-small cell lung carcinoma mouse xenografts carrying mutant p53.

A role for the tumor suppressor gene p53 in many critical cellular pathways, particularly in the cellular response to DNA damage, has been established. These pathways not only include gene transcription, DNA repair, genomic stability, chromosomal segregation and senescence, but also regulation of cell cycle events and the modulation of programmed cell death (apoptosis). For its role in monitoring DNA damage, p53 has been christened "guardian of the genome." Cancer cells are characterized by genetic instability, and mutations in p53 have been found to occur with extremely high frequency in almost all types of human cancers. Indeed, quantitative or qualitative alterations in the p53 gene are suggested to play a role in over half of all human malignancies. The presence of p53 mutations in the most common types of human tumors has been found to be associated with poor clinical prognosis. Moreover, mutant (mt) p53 is rarely found in some of the more curable forms of cancer e.g., Wilms's tumor, retinoblastoma, testicular cancer, neuroblastoma and acute lymphoblastic leukemia.

Numerous studies have reported that the expression of wt p53 has suppressed, both in vitro and in mouse xenograft models, the growth of various malignancies, e.g., prostate, head and neck, colon, cervical and lung tumor cells. It has also been reported that a p53-liposome complex partially inhibited the growth of human glioblastoma and human breast cancer xenografts in mice. In addition, Seung et al. used liposome-mediated intratumoral introduction of a radiation-inducible construct expressing TNF-α to inhibit growth of a murine fibrosarcoma xenograft after exposure to ionizing radiation. However, p53 expression alone, while being able to inhibit tumor growth partially, has not been able to eliminate established tumors in the long-term.

The normal development of mice lacking wtp53 and the observations of a post-irradiation $G_1$ block in p53-expressing cells suggests that wt p53 functions in the regulation of the cell after DNA damage or stress rather than during proliferation and development. Since it appears that many conventional anti-cancer therapies (chemotherapeutics and radiation) induce DNA damage and appear to work by inducing apoptosis, alterations in the p53 pathway could conceivably lead to failure of therapeutic regimens.

Lack of wt p53 function has also been associated with an increase in radiation resistance. The presence of mt p53 and the consequent absence of a $G_1$ block have also been found to correlate with increased radiation resistance in some human tumors and cell lines. These include human tumor cell lines representative of head and neck, lymphoma, bladder, breast, thyroid, ovary and brain cancer.

Based on these considerations, gene therapy to restore wtp53 function in tumor cells should re-establish the p53-dependent cell cycle checkpoints and the apoptotic pathway thus leading to the reversal of the chemo-/radio-resistant phenotypes. Consistent with this model, chemosensitivity, along with apoptosis, was restored by expression of wtp53 in non-small cell lung carcinoma mouse xenografts carrying mtp53. Chemosensitivity of xenografts involving the p53-null lung tumor cell line H1299 and T98G glioblastoma cells and sensitivity of WiDr colon cancer xenografts to cisplatin has been demonstrated. Increased cell killing by doxorubicin or mitomycin C was also shown in SK-Br-3 breast tumor cells by adenoviral transduction of wtp53. However, some conflicting reports indicate that the relationship between p53 expression and chemoresistance may have a tissue or cell type-specific component. The transfection of wtp53 by an adenoviral vector has also been shown to sensitize ovarian and colo-rectal tumor cells to radiation It has also been reported that adenoviral-mediated wtp53 delivery did restore functional apoptosis in a radiation-resistant squamous cell carcinoma of the head and neck (SCCHN) tumor line resulting in radiosensitization of these cells in vitro. More significantly, the combination of intratumorally injected adeno-wtp53 and radiation led to complete and long-term tumor regression of established SCCHN xenograft tumors.

The current invention departs from the conventional use of viral vectors for the delivery of therapeutic molecules for gene therapy, for example as disclosed by Roth et al. (U.S. Pat. No. 5,747,469). These currently used vehicles only have the limited capability of local delivery. Their suitability for intratumoral delivery has been shown not only to be inadequate in reaching all of the cells within the primary tumor mass, but also incapable of reaching sites of metastatic disease.

SUMMARY OF THE INVENTION

In one aspect, the invention provides cell-targeting ligand/liposome/therapeutic molecule complexes for the in vitro or in vivo delivery of therapeutic molecules to targeted cell types. The complexes are useful as delivery vehicles (vectors) for delivering a therapeutic molecule to the target cells. The complexes are useful as vectors for carrying out gene transfer and gene therapy when the therapeutic molecule is, for example, a nucleic acid encoding a therapeutic protein. Specific embodiments relate to folate and transferrin-targeted cationic liposomes for the delivery of a therapeutic molecule to animal (including human) cancer cells that contain folate or transferrin receptors.

In another aspect, the invention provides pharmaceutical compositions comprising a cell-targeting ligand/liposome/therapeutic molecule complex in a pharmaceutically compatible vehicle or carrier. The compositions are formulated for, preferably, intravenous administration to a human patient to be benefitted by the effective delivery of the therapeutic molecule. The complexes are appropriately sized so that they are distributed throughout the body following i.v. administration.

In another aspect, the invention relates to therapeutic methods comprising the administration to a warm-blooded animal (including humans) in need thereof, of a therapeutically effective amount of a pharmaceutical composition comprising a ligand/liposome/therapeutic molecule complex in a pharmaceutically acceptable vehicle. As set forth in detail herein, human cancer treatment via the systemic (e.g. i.v.) administration of a complex comprising a ligand-targeted liposome complex containing a nucleic acid encoding wt p53 is an important embodiment of this aspect of the invention.

Human gene therapy via the systemic administration of pharmaceutical compositions containing targeted liposome/nucleic acid complexes, wherein the nucleic acid comprises a therapeutic gene under the control of an appropriate regulatory sequence, form important examples of the invention. Gene therapy for many forms of human cancers is accomplished by the systemic delivery of folate or transferrin-targeted cationic liposomes containing a nucleic acid encoding wt p53. The data presented herein demonstrates the superior ability of such complexes to specifically target and sensitize tumor cells (due to expression of the wt p53 gene), both primary and metastatic tumors, to radiation and/or chemotherapy both in vitro and in vivo.

Yet another aspect of the invention relates to improvements to the preparation of liposomes, especially ligand-targeted cationic liposomes, whereby liposomes of relatively small, consistent diameters are provided. The consistent, small-diameter liposomes, following intravenous administration, exhibit the ability to circulate in the bloodstream and target both primary tumors and metastases.

The present invention addresses the need to deliver therapeutic molecules systemically with a high degree of target cell specificity and high efficiency. When systemically administered, the complexes of the present invention are capable of reaching, and specifically targeting, metastatic as well as primary disease, when the target cells are human cancer cells. As a result of delivery of the normal, wild-type version of the tumor suppressor gene p53 by means of this system, the inventors demonstrated that the tumors are sensitized to radiation therapy and/or chemotherapy. The high transfection efficiency of this system results in such a high degree of sensitization that not only is there growth inhibition of the cancer but pre-existing tumors and metastases are completely eliminated for an extended period of time. In some instances this period of time is such that the disease may be considered to be cured.

The exceptional efficacy of this system is due in part to the ligand-targeting of the liposome-therapeutic molecule complex. Moreover, the specific cationic and neutral lipids that comprise the liposome complex, as well as the ratio of each, have been varied and optimized so that the efficiency of uptake of the therapeutic molecule would be ideal for the specific target cell type. The ratio of liposome to therapeutic molecule was also optimized for target cell type. This optimization of the liposome-therapeutic molecule complex, in combination with the addition of a targeting ligand, yields substantially improved efficacy when administered in conjunction with radiation or chemotherapies. Those skilled in the art will be able to optimize the complexes for delivering a variety of therapeutic molecules to a variety of cell types.

An important feature of the invention resides in the ability to deliver the therapeutic molecule to the target cell through intravenous, systemic administration. The ability to efficiently target and transfect specific cells following intravenous administration is accomplished by the disclosed combination of selecting an appropriate targeting ligand and optimizing the ratio of cationic to neutral lipid in the liposome. In the case where tumor cells are the target cells, systemic delivery of the ligand-liposome-therapeutic molecule complex allows the efficient and specific delivery of the therapeutic molecule to metastases as well as primary tumor.

The invention is not limited to the use of any specific targeting ligand. The ligand can be any ligand for which a receptor is differentially expressed on the target cell. The presently preferred ligands are folic acid (esterified to a lipid of the liposome) and transferrin, and each of these ligands possesses advantageous properties.

Liposome complexes are capable of penetrating only approximately twenty layers of cells surrounding the blood vessels in a tumor. It has been postulated that wtp53 gene therapy controls cell growth partially through a "bystander" effect, which may be related to the induction of apoptosis by wtp53. This "bystander effect" may account for the effectiveness of the in vivo studies reported herein and may be a contributory factor to the effectiveness of the combination therapy. However, relatively little is known at this time concerning the mechanism and pathway involved in this process for p53. It has been speculated that some as yet unknown apoptotic signal may be contained within the vesicles, which result from apoptosis, and which neighboring cells ultimately phagocytize. Alternatively, this apoptotic signal may be transferred through gap junctions, as is believed to be the case for phosphorylated gancyclovir with the HSV-TK gene. Induction of anti-angiogenic factors may also contribute to the bystander effect.

It has recently been reported that a non-targeted p53-liposome complex partially inhibited the growth of human glioblastoma xenografts in vivo. In addition, Seung et al. (Cancer Res. 55, 5561–5565 (1995) used commercial non-targeted liposome (Lipofectin) mediated intratumoral introduction of a radiation inducible construct containing TNF-α to partially inhibit xenograft growth of a murine fibrosarcoma after exposure to 40 Gy ionizing radiation. Xu et al. (Human Gene Therapy 8, 177–175 (1997)) showed that introduction of 16 μg of p53 DNA in a non-targeted liposome complex was able to partially inhibit the growth of breast cancer xenograft mouse tumors. However, the ligand-directed liposome-p53 complexes of the present invention provide the capacity for target cell specificity, and high transfection efficiency, coupled with systemic administration. The studies reported here are the first to employ such a delivery system in combination with conventional radiation and chemotherapeutic treatment for tumors. While p53 gene therapy alone may not be sufficient to completely eliminate tumors long term, the presently-described combination of liposome-mediated p53 gene therapy and conventional (radiation and/or chemotherapy) therapy was able to achieve not only growth inhibition, but tumor regression, demonstrating a synergistic effect.

The in vivo studies described herein demonstrate that the combination of systemic LipF-p53 or LipT-p53 gene therapy and conventional radiotherapy and/or chemotherapy was markedly more effective than either treatment alone. In the clinical setting, radiation doses of 65 to 75 Gy for gross tumor and 45 to 50 Gy for microscopic disease are commonly employed in the treatment of head and neck cancer. Given the known, adverse side effects associated with high doses of radiation or chemotherapy, sensitization of tumors so as to permit a lowered effective dose of the conventional treatment would be of immense clinical benefit. Furthermore, in the case of radiation, systemic restoration of wtp53 function, resulting in a decrease in the radiation treatment dose found to be effective, would permit further therapeutic intervention for tumors which did reoccur.

In reports using xenograft tumors derived from SCCHN cell lines containing either wtp53 or mtp53 it was noted that introduction of wtp53, via intratumoral administration of an adenoviral vector, was able to inhibit the development of, and induce apoptosis in, these xenograft tumors independent of their endogenous p53 status. Similarly, liposome-mediated introduction of wtp53 into both glioblastoma (RT-2) and breast cancer (MCF-7) xenografts, which have endogenous wtp53, was able to partially inhibit the growth of these tumors. These studies indicate the broad potential of wtp53 gene therapy, irrespective of p53 gene status.

The research underlying the present invention demonstrates that the ligand-cationic liposome-therapeutic molecule complex system can deliver the p53 gene in vivo selectively to tumors of various types, sensitizing them to radiation and chemotherapy. Consequently, systemic wtp53 gene therapy, mediated by the tumor-targeting, relatively safe and efficient ligand-targeted cationic liposome system, in combination with conventional radiotherapy or chemotherapy, may provide a more effective treatment modality not only for primary tumors, but also for those cancers which fail initial therapy.

It also has been demonstrated that the targeted liposome delivery system is capable of delivering small DNA molecules (e.g. antisense oligonucleotides), as well as agents as large as intact viral particles. Delivery of these small (antisense) DNA molecules was also able to sensitize tumor cells to chemotherapeutic agents. Thus, the targeted liposomes of the present invention are widely applicable to the systemic delivery of therapeutic agents.

The invention also relates to methods for preparing ligand-liposome-therapeutic agent complexes. The method by which the complex is formed between the transferrin-liposome and viral particle provides a large number of transferrin molecules upon the surface of the complex and thereby increases the stability of the complex as it travels through the blood stream. Moreover, when the therapeutic molecule is a viral particle, the transferrin liposome may also serve to decrease the immunogenicity of the virus by blocking viral antigens.

Using the present invention, the inventors have demonstrated a remarkable effect not only in controlling cell growth, in particular tumor cell growth, but also in effecting tumor remission long-term. Tumor cell formation and growth, also known as transformation, describes the formation and proliferation of cells that have lost their ability to control cell division, that is, they are cancerous. A number of different types of transformed cells can serve as targets for the methods and compositions of the present invention, such as: carcinomas, sarcomas, melanomas, and a wide variety of solid tumors and the like. Although any tissue having malignant cell growth may be a target, head and neck, breast, prostate, pancreatic, glioblastoma, cervical, lung, liposarcoma, rhabdomyosarcoma, choriocarcinoma, melanoma, retinoblastoma, ovarian, gastric and colorectal cancers are preferred targets.

It is further contemplated that the invention can also be used to target non-tumor cells for delivery of a therapeutic molecule. While any normal cell can be a target, the preferred normal targets are dendritic cells, endothelial cells of the blood vessels, lung cells, breast cells, bone marrow cells, and liver cells.

It is disclosed herein that, when delivered systemically, the ligand-targeted, optimized cationic liposomal-therapeutic molecule complex was able to specifically target and markedly sensitize tumor cells to radiation and/or chemotherapy resulting in substantial growth inhibition and tumor regression. The ligand-targeted, optimized cationic liposomal-therapeutic molecule complex may be delivered via other routes of administration such as intratumoral, aerosol, percutaneous, endoscopic, topical, intralesional or subcutaneous administration.

The invention provides, in certain embodiments, methods and compositions for the highly target cell-specific and efficient delivery, via systemic administration, of a ligand-targeted, liposomal-therapeutic molecule complex. Examples of therapeutic molecules include a gene, high molecular weight DNA, plasmid DNA, an antisense oligonucleotide, peptides, ribozymes, peptide nucleic acids, a chemical agent such as a chemotherapeutic molecule, or any large molecule including, but not limited to, DNA, RNA, viral particles, growth factors cytokines, immuno-modulating agents and other proteins, including proteins which when expressed present an antigen which stimulates or suppresses the immune system.

Recently, efficient methods for long term expression of gene therapy vectors have been described (Cooper, et al, 1997; Westphal et al., 1998; Calos, 1996 and 1998). These vectors can be useful for extending and/or increasing the expression levels of the disclosed liposomal delivery system. Several autonomous and episomal vector systems are disclosed in U.S. Pat. Nos. 5,707,830 (Calos, M. P., 13 Jan. 1998); 5,674,703 (Woo, S., et al., 7 Oct. 1997) and 5,624,820 (Cooper, M. J., 29 Apr. 1997) each of which is incorporated by reference herein. Calos relates to Epstein Barr virus-based episomal expression vectors useful in autonomous replication in mammalian cells. Woo et al. relates to papilloma virus-based episomal expression vectors for replication in animal cells. Cooper et al. relates to vectors containing at least one papovavirus origin of replication and a mutant form of papovavirus large T antigen for long term episomal expression in human gene therapy.

When the therapeutic molecule is the p53 gene or an antisense oligonucleotide, delivery via the complex of the invention results in the sensitization of a cell or cells, such as a malignant cell or cells, to either radiation or a chemotherapeutic agent such that the cells are killed via the combination therapy. Malignant cells are defined as cells that have lost the ability to control the cell division cycle as leads to a transformed or cancerous phenotype. In addition to malignant cells, cells that may be killed using the invention include e.g., undesirable but benign cells, such as benign prostatic hyperplasia cells, over-active thyroid cells, lipoma cells, as well as cells relating to autoimmune diseases such as B cells that produce antibodies involved in arthritis, lupus, myasthenia gravis, squamous metaplasia, dysplasia and the like.

The ligand-liposome-therapeutic molecule complex can be formulated under sterile conditions within a reasonable time prior to administration. If the therapeutic molecule is one which provides enhanced susceptibility to another therapy (such as enhanced susceptibility of cancer cells to chemotherapy or radiation therapy), such other therapy may be administered before or subsequent to the administration of the complex, for example within 12 hr to 7 days. A combination of therapies, such as both chemotherapy and radiation therapy, may be employed in addition to the administration of the complex.

The terms "contacted" or "exposed" when applied to a cell are used herein to describe the process by which a therapeutic molecule is delivered to a cell, or is placed in direct juxtaposition with the target cell, so that it can effectively interact with the cell to bring about a desired benefit to the cell or the host animal.

Wherein the complexes of the invention are used as an element of a combination therapy for, for example, human cancer treatment, they may be used in combination with a wide variety of therapies employed in the treatment of human or animal cancer. Such therapies include the administration of chemotherapeutic agents and radiation therapies such as gamma-irradiation, X-rays, UV irradiation, microwaves, electronic emissions and the like. Chemotherapeutic agents such as doxorubicin, 5-fluorouracil (5FU), cisplatin (CDDP), docetaxel, gemcitabine, pacletaxel, vinblastine, etoposide (VP-16), camptothecia, actinomycin-D, mitoxantrone and mitomycin C can be employed in combination therapies according to the present invention.

A variety of different types of potentially therapeutic molecules can be complexed with the cell-targeted ligand/liposome complexes of the invention. These include, but are not limited to, high molecular weight DNA molecules (genes), plasmid DNA molecules, small oligonucleotides, RNA, ribozymes, peptides, immunomodulating agents, peptide nucleic acids, viral particles, chemical agents such as per se known chemotherapeutic agents and drugs, growth factors, cytokines and other proteins including those which, when expressed, present an antigen which stimulates or suppresses the immune system. Therefore, in addition to gene therapy, the present invention can be used for immunotherapy or for the targeted delivery of drugs.

Diagnostic agents also can be delivered to targeted cells via the disclosed complexes. Agents which can be detected in vivo after administration to a multi-cellular organism can be used. Exemplary diagnostic agents include electron dense materials, magnetic resonance imaging agents and radiopharmaceuticals. Radionuclides useful for imaging include radioisotopes of copper, gallium, indium, rhenium, and technetium, including isotopes $^{64}$Cu, $^{67}$Cu, $^{111}$In, $^{99m}$Tc, $^{67}$Ga or $^{68}$Ga. Imaging agents disclosed by Low et al. (U.S. Pat. No. 5,688,488) are useful in the present invention, and that patent is incorporated by reference herein.

The ligand-liposome composition of the invention, which will be complexed with the therapeutic molecule, can be comprised of a ligand, a cationic lipid and a neutral or helper lipid, where the ratio of cationic lipid to neutral lipid is about 1:(0.5–3), preferably 1:(1–2) (molar ratio). The ligand can be bound, e.g. via chemical coupling, to the neutral lipid and mixed with cationic lipid and neutral lipid at a molar ratio of about (0.1–20):100, preferably (1–10):100, and more preferably (2.5–5):100 (ligand-lipid:total lipids), respectively. The ligand-liposome will be mixed with DNA or other therapeutic molecules to form a complex. The DNA to lipid ratios will be in a range of about 1:(0.1–50), preferably about 1:(1–24), and more preferably about 1:(6–16) µg/nmol. For antisense oligonucleotides, the complex will be formed by mixing the liposome with oligonucleotides at a molar ratio of about (5–30):1 lipid:oligonucleotide, preferably about (10–25):1, and most preferably about 10:1.

Alternatively, as in the case of transferrin, the ligand can simply be mixed with the cationic and neutral lipids. In this instance, the cationic liposomes will be prepared at a molar ratio of cationic lipid to neutral lipid of about 1:(0.5–3), preferably 1:(1–2). Transferrin will be mixed with the cationic liposomes and then DNA or other therapeutic molecules. The DNA/Lipid/Tf ratios will be in the range of about 1:(0.1–50):(0.1–100) µg/nmol/µg, preferably about 1:(5–24):(6–36), and more preferably about 1:(6–12):(8–15), respectively.

Another unique feature of the complexes according to the invention is their evenly distributed relatively small size (mean diameter less than about 100 nm, preferably less than about 75 nm, and more preferably about 35–75 nm (50 nm average) diameter). To reach the target tumor, the complexes must be resistant to degratory agents encountered in vivo, and also must be capable of passing through the blood vessel (capillary) walls and into the target tissue. The complexes of the present invention exhibit high resistance to degradation by elements present in serum. The permeable size of the capillaries in tumors is usually 50–75 nm, and the complexes which are less than about 75 nm diameter can pass easily through the capillary wall to reach the target. Based upon transmission electron microscopy, it appears that a unique onion-like layered structure of the LipF-DNA and LipT-DNA complex plays an important role in the small size and, consequently, high transfection efficiency of the complex of the invention observed in vitro and, in particular, in vivo.

The ligand can be any molecule that will bind to the surface of the target cell, but preferentially to a receptor that is differentially expressed on the target cell. Two particularly preferred ligands are folate and transferrin. The cationic lipid can be any suitable cationic lipid, but dioleoyltrimethylammonium-propane (DOTAP) and DDAB are preferred. The neutral lipid can be any neutral lipid, and preferred neutral lipids are dioleoylphosphatidylethanolamine (DOPE) and cholesterol.

A number of in vitro parameters may be used to determine the targeting and delivery efficiency of the composition so that particular complexes can be optimized to deliver a desired therapeutic molecule to the selected target cell type. These parameters include, for example, the expression of marker genes such as the β-galactosidase or luciferase genes, immunohistochemical staining of target cells for the delivered protein, Western blot analysis of the expression of the protein product of the delivered gene, down-modulation of the target gene due to a delivered anti-sense or other inhibitory oligonucleotide, as well as increased sensitization of the target cells to radiation and/or chemotherapeutic agents.

In a preferred embodiment, it is contemplated that the p53 expression region will be positioned under the control of a strong constitutive promoter such as an RSV or a CMV promoter. Currently, a particularly preferred promoter is the cytomegalovirus (CMV) promoter.

The methods and compositions of the present invention are suitable for targeting a specific cell or cells in vitro or in vivo. When the target cells are located within a warm-blooded animal, e.g. head and neck, breast, prostate, pancreatic or glioblastoma cells, the ligand-liposome-therapeutic molecule complex will be administered to the animal in a pharmacologically acceptable form. A "pharmacologically acceptable form", as used herein refers to both the formulation of the ligand-liposome-therapeutic molecule complex that may be administered to an animal, and also the form of contacting an animal with radiation, i.e. the manner in which an area of the animals body is irradiated, e.g. with gamma-irradiation, X-rays, UV-irradiation, microwaves, electronic emissions and the like. The use of DNA damaging radiation and waves is known to those skilled in the art of radiation therapy.

The present invention also provides improved methods for treating cancer, both primary and metastatic, that, generally, comprise administering to an animal or human patient in need thereof a therapeutically effective combination of a ligand-liposome-therapeutic molecule (e.g. p53 gene) complex, and a therapy such as radiation or chemotherapy.

The complex will generally be administered to the animal, usually systemically, in the form of a pharmaceutically acceptable composition. In the preferred embodiment, the composition would be delivered systemically through an intravenous route. However, other routes of administration such as aerosol, intratumoral, intralesional, percutaneous, endoscopic, topical or subcutaneous may be employed.

The high degree of tumor cell specificity and tumor targeting ability of the invention was demonstrated by the expression of a reporter gene after systemic delivery by the folate/transferrin-liposome-β-Gal gene complex. β-galactosidase expression was evident in up to 70% of the xenografts of various human tumor cells, including JSQ-3, DU145 and MDA-MB-435, while normal tissues and organs, including the highly proliferative gut and bone marrow, showed no evidence of transfection. The highly efficient tumor targeting ability of the invention was also evident in these experiments where metastases, and even micro-metastases as small as a few cells, were found to have been specifically transfected after systemic delivery of the complex.

The surprising success of the present invention is evidenced by the finding that systemic delivery of either folate-liposome-wtp53 gene or transferrin-liposome-wtp53 gene, in combination with either radiation or chemotherapy, yielded profound results in studies using a nude mouse model. The high efficiency of this system results in such a high degree of sensitization of JSQ-3 and DU145 human xenograft tumors to radiation that not only is there growth inhibition of the cancer but, in some experiments, the pre-existing tumors and metastases were completely eliminated for an extended period of time. In some instances this period of time (more than one year disease-free) is such that the disease may be considered to be cured. Human breast cancer MDA-MB-435 and human pancreatic cancer PANC I nude mouse xenograft tumors were also shown to be highly sensitized by the systemic administration of either folate-liposome-wtp53 or transferrin-liposome-wtp53 to chemotherapeutic agents including doxorubicin, cisplatin, docetaxel or gemcitabine.

As used herein, the term "transfection" is used to describe the targeted delivery of a therapeutic molecule to eukaryotic cells using the ligand-liposome complex of the invention and entry of the therapeutic molecule into the cell by various methods, such as receptor mediated endocytosis. The target cell may be preferentially selected by the ligand of the complex such that the ligand will bind to a receptor that is differentially expressed on the surface of the target cell.

Preferred pharmaceutical compositions of the invention are those that include, within a pharmacologically acceptable solution or buffer, a complex consisting of a ligand, a cationic-neutral liposome and a therapeutic molecule.

Still further embodiments of the present invention are kits for use in the systemic delivery of a therapeutic molecule by the ligand-liposome complex, as may be formulated into therapeutic compositions for systemic administration. The kits of the invention will generally comprise, in separate, suitable containers, a pharmaceutical formulation of the ligand, of the liposome and of the therapeutic molecule. In the preferred embodiment the ligand would be either folate or transferrin, the liposome would consist of a cationic and a neutral lipid and the therapeutic molecule would be either a construct carrying wtp53 under control of the CMV promoter, or an antisense oligonucleotide. The three components can be mixed under sterile conditions and administered to the patient within a reasonable time frame, generally from 30 min to 24 hours, after preparation.

The components of the kit are preferably provided as. solutions or as dried powders. Components provided in solution form preferably are formulated in sterile water-for-injection, along with appropriate buffer(s), osmolarity control agents, antibiotics, etc. Components provided as dry powders can be reconstituted by the addition of a suitable solvent such as sterile water-for-injection.

DETAILED DESCRIPTION OF THE PREFERRED EMBODIMENTS

The present invention uses systemic administration of a ligand/cationic liposomal delivery complex for tumor-targeted delivery of a therapeutic molecule via receptor-mediated endocytosis. In one of the preferred embodiments, the ligand-targeted liposomes are used to deliver a therapeutic molecule comprising a gene encoding wild-type (wt) p53. The therapeutic gene is targeted and effectively delivered to tumor cells, resulting in the restoration of the normal p53 gene function that many tumors lack. This restoration has a profound effect on the ability to treat the tumors. In another preferred embodiment, the therapeutic molecules being delivered are antisense oligonulceotides directed against genes in the cell growth pathway. Down-modulation of these genes results in sensitization of the tumor cells and xenografts to radiation and chemotherapeutic agents. In yet another embodiment, the "therapeutic molecule" is an intact viral vector (e.g. an adenoviral or retroviral particle containing a therapeutic nucleic acid) which is delivered to the targeted cell via the ligand/liposome complex.

In another aspect, the invention provides compositions and methods for accomplishing gene therapy to restore wtp53 function in tumor cells, leading to the reversal of chemo-/radio-resistant phenotypes and consequently improving the ability to treat the tumor via chemo- and/or radiation therapy.

The present invention provides a new and improved method for accomplishing cancer gene therapy by providing a systemic delivery system ("complex") that specifically targets tumor cells, including metastases, and results in a more effective cancer treatment modality. This method uses a ligand-directed cationic liposome system to deliver a therapeutic molecule to the tumor cells. In one of the preferred embodiments, this therapeutic molecule is wtp53. The inclusion of a cell-targeting ligand (e.g. the folate or transferrin ligand) in the liposome-DNA complex takes advantage of the tumor-targeting facet and receptor-mediated endocytosis associated with the ligand to introduce wtp53 efficiently and specifically to the tumor cells in vivo as well as in vitro. The consequence of this restoration of wtp53 function is an increase in sensitization to conventional radiation and chemo-therapies, thereby increasing their efficacy and/or reducing the total dose thereof.

The exemplified liposome compositions are based upon the cationic lipid DOTAP and fusogenic neutral lipid DOPE conjugated (e.g. esterified) to either folic acid (to provide a folate ligand thereon) or simply mixed with iron-saturated transferrin. The ratio of lipids themselves, as well as the lipid:DNA ratio, will be optimized for in vivo delivery, as well as for different tumor cell types, e.g. adenocarcinoma vs. squamous cell carcinoma. In vitro studies demonstrated that the addition of the ligand substantially increased the transfection efficiency for tumor cells when compared to the liposome alone, even in the presence of high levels of serum. Transfection of wtp53 by this method resulted in substantial radiosensitization of a previously radiation resistant SCCHN cell line in vitro.

The in vivo tumor targeting capability of this system was assessed using the β-galactosidase reporter gene in three different types of cancer—SCCHN, breast cancer and prostate cancer. These studies demonstrated that after intravenous administration of the complexes, only the tumors were transfected, with an efficiency between 50 and 70%, while normal organs and tissues, including the highly proliferative bone marrow and intestinal crypt cells, showed no signs of reporter gene expression. Some ligand-liposome-DNA complex was evident in macrophages. Very significantly, even micro-metastases in the lung, spleen and lymph nodes showed evidence of highly efficient and specific transfection.

When the systemically delivered ligand-liposome wtp53 complex was administered to mice bearing radiation resistant human SCCHN xenografts, and followed with radiation therapy, the tumors completely regressed. Histological examination of the area of the former tumor showed only normal and scar tissue remaining, with no evidence of live tumor cells. This was in contrast to the tumors from animals treated only with the ligand-liposome-p53 complex or only with radiation. In these animals some cell death was evident. However, nests of live tumor cells remained, resulting in the regrowth of the tumors in these animals. Strikingly, no recurrence of the tumors was evident in the animals receiving the combination therapy, even one year after the end of treatment. Similar results were observed in mice bearing human prostate tumor xenografts with radiation and chemotherapeutic agents, as well as with human breast cancer and pancreatic cancer xenografts with chemotherapeutic agents. Consequently, this system is viewed as providing a more effective form of cancer therapy.

Therefore, the present invention represents a significant improvement upon current experimental cancer therapies, such as local injection of adenoviral vectors carrying a therapeutic molecule such as p53, which are frequently incapable of administering a therapeutic molecule to the entire tumor tissue (primary tumor mass). Local delivery also lacks the capability of reaching distant metastases. The specific targeting ability provided by the present invention is also advantageous since it reduces side effects that can be associated with wide spread non-specific uptake of the therapeutic molecule.

The uptake of the ligand-liposome-therapeutic molecule complex by the target cells will, when administered in conjunction with adjuvant therapies, and when the target cells are cancer cells, not only decrease the rate of proliferation of these cells but actually result in increased tumor cell death and long-term tumor regression. The delivery system of the invention strongly portends a prolongation of patient survival.

Even though the invention has been described with a certain degree of particularity, it is evident that many alternatives, modifications, and variations will be apparent to those skilled in the art in light of the present disclosure. Accordingly, it is intended that all such alternatives, modifications, and variations which fall within the spirit and the scope of the invention be embraced by the defined claims.

The following examples are included to demonstrate preferred embodiments of the invention.

EXAMPLE 1

Construction of p53 Expression Vector

This example describes the construction of p53 expression vectors. The methods used are those commonly known to those skilled in the art. The invention is not limited to any particular expression vector, however.

Figure 1A:
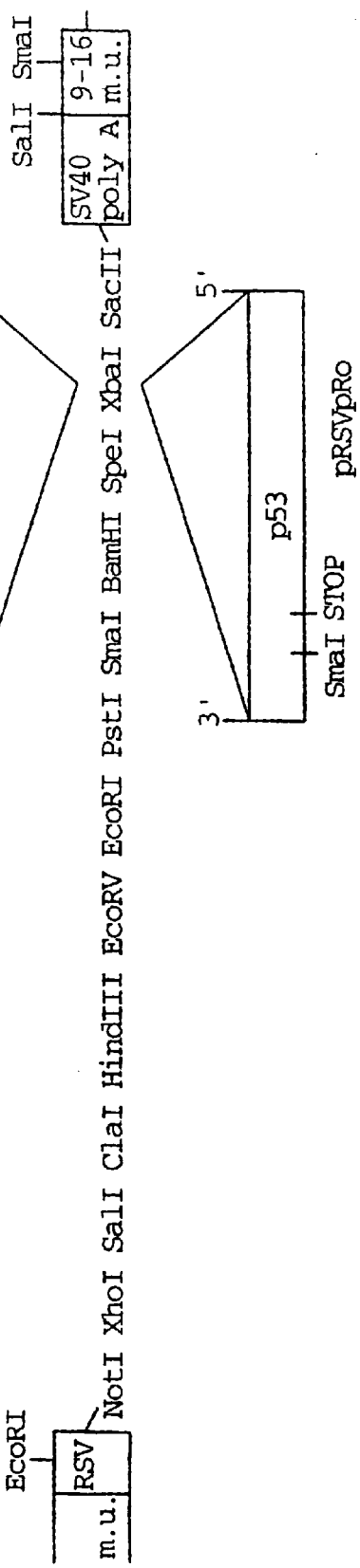
FIGS. 1A and 1B show the adenoviral shuttle plasmids pRSVp53, pRSVpRo, pCMVp53 and pCMVpRo that contain the sense and anti-sense cDNA of p53.
Figure 1B:
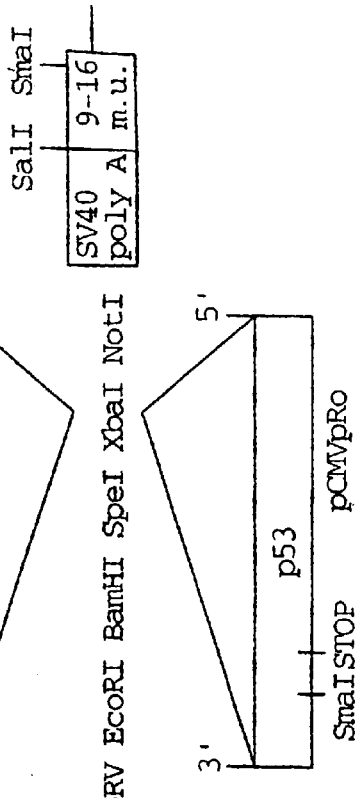

The adenoviral shuttle plasmids pRSVp53, pRSVpRo, pCMVp53 and pCMVpRo that contain the sense and antisense cDNA of p53 are shown in FIG. 1. These plasmids were constructed by cloning the 1.7 Kb XbaI p53 cDNA fragment into an adenoviral shuttle vector. Davidson, et al., Experimental Neurobiology 125, 258–267 (1994) is incorporated by reference herein for the purpose of disclosing the preparation of such shuttle vectors. Orientation was determined by restriction digest and confirmed by DNA cycle sequencing. The plasmids were expanded in *E. coli* DH5α and purified by Qiagen Plasmid Mega/Giga Kits (Qiagen). The purified plasmids were quantified spectrophotometrically with $A_{260}/A_{280}$ values approximately 1.90. Agarose gel (0.8%) electrophoresis confirmed that more than 95% of plasmid DNA was supercoiled.

EXAMPLE 2

Synthesis of Ligand-liposome-DNA Complexes

This example describes one method suitable for the production of the ligand-liposome-therapeutic molecule complex, where the therapeutic molecule is plasmid DNA. 15 mmol dioleoylphosphatidylethanolamine (DOPE) in dry chloroform was reacted with 20 mmol N-hydroxysuccinimide ester of folic acid (see Lee, R. J., et al., J. Biol. Chem. 269, 3198–3204 (1994), which is incorporated by reference herein for the purpose of disclosing such procedures) in the presence of 20 mmol triethylamine for 4 hours at room temperature, then washed with PBS 3 times to obtain folate-DOPE in chloroform. Thin-layer chromatography (chloroform: methanol: acetic acid, 80:20:5) revealed that more than 95% of DOPE (Rf=0.65–0.70) was converted to folate-DOPE (Rf=0.90–0.95). LipF(A) was prepared as follows: a chloroform solution of 5 μmol dioleoyltrimethylammonium-propane (DOTAP), 5 μmol DOPE and 0.1 μmol folate-DOPE were mixed together in a round-bottom flask, and the chloroform evaporated under reduced pressure. 10 ml sterile water was added to the flask to suspend the lipids, then sonicated for 10 min in a bath-type sonicator at 4° C. The final concentration of LipF(A) was 1 nmol/μl total lipids. The LipF(A)-DNA complex for in vitro use was prepared by mixing equal volumes of LipF(A) and DNA in serum-free RPMI-1640 folate free medium (Life Technologies, Inc.) and incubating at room temperature, with frequent rocking, for 15–30 minutes. DNA retardation assay showed that at the ratio of 1 μg DNA: 8–10 nmol LipF(A), almost all of the added DNA was complexed with lipids. For in vivo experiments, plasmid DNA (diluted in HEPES buffer, pH 7.4 based upon the total amount of DNA/mouse) was mixed with LipF(A)(in water) at the ratio of 1 μg DNA/8–12 nmol lipids, and incubated for 15–30 minutes at room temperature with frequent rocking. A 50% dextrose solution was added to reach a final concentration of 5% dextrose, mixed by inversion and checked for signs of precipitation (the presence of particulate matter or cloudiness). In both cases, the LipF (A)-DNA complexes were found to be stable for up to 24 hour at 4° C. in the dark, without substantial loss of transfection efficiency.

Cationic liposomes consisting of dioleoyl trimethylammonium propane (DOTAP) and dioleoyl phosphatidylethanolamine (DOPE) (Avanti Polar Lipids, Inc., Alabaster, AL) were prepared as above. The final concentration of liposomes was 2 nmol/ul. Holo-transferrin (Tf, iron-saturated, Sigma) was dissolved in pure water at 5 mg/ml. The Tf-liposome-DNA complex for in vitro experiments was prepared as described by Cheng, P. W., Human Gene Therapy 7, 275–282 (1996) (which is incorporated herein by reference for the purpose of illustrating liposome preparation) with modifications. In brief, 12 nmol of liposomes were added to 18 mg Tf in 100 μl serum-free EMEM and incubated for 5–15 min at room temperature with frequent rocking. This solution was then mixed with 1.2 μg plasmid DNA in 100 μl serum-free EMEM and incubated for 15–30 minutes at room temperature with frequent rocking. The prepared Tf-liposome (designated LipT(A))-DNA complex was used for in vitro cell transfection freshly within 1 hour of preparation, although it was found to be stable for at least 24 hours with the same transfection efficiencies. Agarose gel electrophoresis was employed to assess the DNA retardation by LipT(A). Greater than 90% of the DNA was found to be complexed to the liposome. For in vivo studies, the liposome and transferrin (in water) were mixed and incubated for 5–15 minutes at room temperature with frequent rocking. This solution was then mixed with DNA (in HERPES buffer pH=7.4) and incubated for 15–30 minutes at room temperature with frequent rocking. A 50% dextrose solution was added to reach a final concentration of 5% dextrose, mixed by inversion and checked for signs of precipitation (the presence of particulate matter or cloudiness). In both cases, the LipT(A)-DNA complexes were found to be relatively stable for up to 24 hours at 40° C. in the dark, without substantial loss of transfection efficiency.

EXAMPLE 3

Folate-Liposome Optimization by X-Gal Staining

This example describes the optimization of the folate cationic-liposome (LipF) complex of the invention for squamous cell carcinoma of the head and neck (SCCHN). To optimize the transfection efficiency for SCCHN cell line JSQ-3, the *E. coli* LacZ gene, driven by an SV40 promoter in plasmid pSVb, was employed as a reporter. Transfection efficiency was calculated based upon the percent of X-Gal stained cells. As shown in Table 1, the presence of folate ligand in the complex substantially increased the reporter gene expression. The non-ligand linked cationic liposome (Lip(A)) gave a transfection efficiency of 10%–20% in JSQ-3, in vitro, while LipF(A) resulted in 60%–70% of the cells expressing the β-galactosidase gene. The addition of 1 mM free folic acid to the cells prior to transfection was able to block the folate receptors on the cells, thereby reducing the transfection efficiency to 20%, similar to that observed with LipF(A). These results demonstrate that using folate as a ligand increases the transfection efficiency of cationic liposomes, and that this effect is mediated by the folate receptor. Based upon a recent report that X-gal staining may underestimate the extent of β-galactosidase gene expression by 20% or higher, it is conceivable that the transfection efficiency with the ligand-targeted liposome may actually exceed the 70% stated above.

TABLE 1

In vitro transfection efficiencies for LipF(A) in JSQ-3 cells:*

| Transfected by | Without Serum | With Serum |
| --- | --- | --- |
| PSVb alone | 0% | 0% |
| Lip(A)-pSVb | <20% | <10% |
| LipF(A)-pSVb | 60%–70% | 40%–50% |
| LipF(A)-pSVb + 1 mM Folate** | 15%–20% | 10%–20% |

*60% confluent JSQ-3 cells, cultured in folate-free medium in a 24-well plate were transfected for 5 hours with 0.5 ml of transfection solution containing 1.2 μg of pSVb. After an additional 2 days in culture, the cells were fixed and stained with X-gal. Transfection efficiency was calculated as percent of blue stained cells.
**Folate was added immediately before transfection.

EXAMPLE 4

Optimization of LipT(A) System by Luciferase Assay

This example describes the optimization of the transferrin cationic-liposome [LipT] complex of the invention for squamous cell carcinoma of the head and neck (SCCHN). The LipT(A) system was optimized for JSQ-3 transfection using the luciferase assays. The firefly luciferase gene driven by cytomegalovirus (CMV) promoter in plasmid pCMVLuc was employed as the reporter gene (Promega). $5 \times 10^4$ JSQ-3 cells/well were plated in a 24-well plate. 24 hours later, the cells were washed once with EMEM without serum, 0.3 ml EMEM without serum or antibiotics was added to each well. The freshly prepared Tf-liposome-pCMVLuc (LipT(A)-Luc) complex containing different amounts of plasmid DNA up to 1.0 μg in 0.2 ml EMEM was added to the cells. After a 5-hour incubation at 37° C. and 5% $CO_2$, 0.5 ml EMEM supplemented with 20% fetal bovine serum and 1 μg/ml hydrocortisone were added to each well. 24 hours later, the cells were washed once with PBS, lysed with 100 μl/well 1X Reporter Lysis Buffer (Promega), and the expressed luciferase activities were measured with Luciferase Assay System (Promega) on a Luminometer. A recombinant firefly luciferase (Promega) standard was used during each measurement for converting the luminometer readings of relative light unit (RLU) to the equivalent amount of luciferase expressed. Protein concentration of cell lysate was measured using the Bio-Rad DC Protein Assay Kit (Bio-Rad Laboratories). The results were expressed as μg of luciferase equivalent per mg of total protein. JSQ-3 cells were transfected with LipT(A)-pCMVLuc (LipT(A)-Luc) at different DNA/Lipid ratios in the complex. Transferrin substantially enhanced the transfection efficiency of cationic liposomes. Under optimal condition, i.e., DNA/Lipid/Tf ratio at 1 ug/10 nmol/12.5 ug, luciferase was expressed at 12.5±1.1 ug/mg total protein, or 1.25% total protein, 7- to 10-fold more than liposome alone without transferrin.

EXAMPLE 5

In Vitro Transfection of JSQ-3 Cells by LipT(A)-pSVb

This example uses a quantitative β-galactosidase colorimetric assay, as described in Example 3, to demonstrate the increased transfection efficiency of the transferrin-liposome complex of the invention. Purified β-galactosidase (Boehringer) was used as standard. The results were expressed as milliunits (mU) of β-galactosidase equivalent per mg of total protein. For histochemical studies of Tf-liposome-pSVb transfection, 60% confluent JSQ-3 cells in a 24-well plate were transfected for 5 hours with 1.2 μg of pSVb with or without LipT(A). After an additional 2 days in culture, the cells were fixed and stained with X-gal. Transfection efficiency was calculated as percentage of blue-stained cells. In quantitative β-galactosidase assay, the JSQ-3 cells transfected at the optimal condition, with 0.5 ug DNA/$10^5$ cells of LipT(A)-pSVb, expressed 15.04±0.60 mU/mg total protein of β-galactosidase without serum, and 10.95±0.15 mU/mg with serum. In histochemical studies, transfection with LipT(A)-pSVb resulted in 70%–80% of the cells being transfected. The presence of serum during transfection slightly reduced transfection efficiency, but even with serum, 40–50% of the cells stained blue, while cationic liposome without ligand gave only 10–20% efficiency. These results demonstrated that using Tf as a ligand substantially increased the transfection efficiency of cationic liposomes, even in the presence of serum.

EXAMPLE 6

Selective Tumor and Metastases Targeting by the Ligand-liposome Complex In Vivo This example demonstrates the ability of the folate or transferrin complexed liposome to selectively target tumor tissue in vivo. Xenografts were induced by the subcutaneous injection of JSQ-3, MDA-MB-435 or DU145 cells. $2.5 \times 10^6$ (JSQ-3) or $5 \times 10^6$ (Du145) cells were injected on the lower back above the tail of 4–6 week old female athymic nude (NCr nu-nu) mice. $1 \times 10^7$ MDA-MB-435 cells were injected subcutaneously into the mammary fat pad of the mice. For the metastases model, $1 \times 10^6$ JSQ-3 or MDA-MB-435 cells were intravenously injected, via the tail vein, into the animals. LipF(A)-pSVb or LipF(D)-pSVb was prepared as described in Example 2. LipF-pSVb or pSVb plasmid alone (in 5% dextrose) were injected intravenously via the tail vein, at 25 μg of plasmid DNA/300 μl/animal. Two days and 10 days after DNA injection, the tumors as well as mouse organs were excised, cut into 1 mm sections, washed once with PBS, and fixed with 2% Formaldehyde-0.2% glutaraldehyde for 4 hours at room temperature. The fixed tumor sections were washed 4 times, each for 1 hr, and stained with X-Gal solution plus 0.1% NP-40 (pH 8.5) at 37° C. overnight The stained tumor sections were embedded and sectioned using normal histological procedures and counterstained with nuclear fast red. Four sections per tumor were examined to evaluate the β-galactosidase gene expression, as indicated by the blue stained cells.

LipF(A)-pSVb or pSVb alone was intravenously injected into nude mice bearing JSQ-3 xenografts. Within 48 hours, the LipF(A)-pSVb injected group showed reporter gene expression in the tumors with an in vivo transfection efficiency of approximately 40–50%. In contrast, with pSVb plasmid alone, less than 1% of the tumor cells stained for the β-galactosidase reporter gene. Ten days after i.v. administration of LipF(A)-pSVb, both the percentage and intensity of blue staining in the tumors were substantially reduced, indicating that the LipF(A)-mediated systemic transfection is transient. Vital organs in LipF(A)-pSVb injected mice showed only macrophages such as Kupffer cells (liver) or dust cells (lung) staining blue, while the hepatocytes and lung alveoli cells themselves remained unstained. The selectivity of tumor targeting was also shown where the tumor was found invading muscle. The LipF(A)-pSVb transfected only the tumor while the muscle cells remained unstained. More significantly, the highly proliferating bone marrow and intestinal crypt cells were apparently not transfected. Both the crypt cells and the bone marrow showed little if any (<1%) evidence of reporter gene staining. The lack of LipF(A)-pSVb transfection in the bone marrow and crypt cells demonstrates that targeting is not a nonselective, cell proliferation effect, but appears to be targeting the tumor cells. This is further demonstrated by no staining being evident in the endothelial cells of blood vessels, although they were exposed to the highest concentration of the LipF(A)-pSVb complex as it travels through the blood stream. In addition, no staining was evident in the lymphoblastic growth centers in the spleen even though the dendritic cells displayed B-galactosidase staining.

A major problem in cancer recurrence and treatment is metastases. To test for the ability of the LipF(A) complex to target tumor cells apart from the subcutaneous xenograft, JSQ-3 cells were i.v. injected into nude mice. By two weeks after the injection, simulated metastases (islands of tumor cells in multiple organs) formed. Animals were then injected intravenously with LipF-pSVb and the simulated metastases examined for β-galactosidase expression. Extensive X-gal staining was seen in a metastasis found in a thoracic lymph node. In this section, a blood vessel (BV) was found surrounded by the metastatic tumor cells. Although the tumor cells exhibited strong X-gal staining 20–25 layers from the blood vessel, no reporter gene expression was evident in the endothelial cells of the blood vessel, even though they were exposed to the highest concentration of the LipF(A)-pSVb complex as it traveled through the blood stream. These results confirmed the tumor-selective nature of the LipF(A) complex and demonstrated that metastases as well as primary tumors can be targeted via folate-containing liposomes.

To assess the breadth of applicability this folate-linked, liposome mediated delivery system to cancers other than SCCHN, experiments were also performed with xenografts of other human tumor cell lines including human breast carcinoma cell lines MDA-MB-435, Hs578T, and human prostate cancer cell line DU145, which also carry mt p53. Here too, a single i.v. injection of LipF(A)-pSVb demonstrated tumor selectivity. A high level of β-galactosidase expression was seen in the MDA-MB-435 mammary fat pad tumor while the adjacent normal muscle tissue remained unstained. Reporter gene expression was not detected in non-tumor tissues or normal organs including intestinal crypt cells and hepatocytes, while subcutaneous mammary fad pad xenografts showed an average of 50–70% blue staining. Two weeks after i.v. injection of MDA-MB-435 cells, the LipF(A)-pSvb was systemically delivered via a single tail vein injection. Even small simulated breast metastases in the lung displayed a high level of staining, and the adjacent normal lung tissue remained completely unstained.

Mice bearing DU145 xenografts were given a single i.v. injection of LipF(B)pSVb. Tumors in these mice also showed reporter gene expression representing an in vivo transfection efficiency of at least 40–50%, a value about 50-fold higher than achieved with plasmid alone.

The transferrin-liposome, liposome-pSVb and pSVb DNA complexes were prepared in sterile 5% dextrose instead of HBSS, at a ratio of 1 μg DNA/10 nmol liposome/12.5 μg transferrin. The nude mouse tumor model was established by subcutaneous injection of JSQ-3 cells in the flank of 4–6 weeks old female nude mice. 30 μg pSVb DNA complexed with Tf-liposome in 300 ml volume were injected into each mouse via tail vein with 1 cc syringe and a 30 G needle. In the control groups, liposome-pSVb or pSVb DNA without liposome were injected. At 2 days, the tumors in mice injected with LipT(A)-pSVb showed reporter gene expression representing an in vivo transfection efficiency of approximately 20–40%. In contrast, with pSVb plasmid alone, without liposome, less than 1% of the tumor cells stained for reporter gene expression. Ten days after intravenous administration of LipT(A)-pSVb, both the percentage of positive cells and the intensity of blue staining in the tumors were substantially reduced, indicating that the LipT(A)-mediated systemic transfection was transient. Vital organs in mice injected with LipT(A)-pSVb showed staining of only macrophages (such as dust cells of the lung and Kupffer cells of the liver), whereas the hepatocytes and lung alveolar cells remained unstained. No staining was evident in the lymphoblastic growth centers in the spleen although the dendritic cells displayed modest staining. In summary, the histological staining indicated that delivery of the reporter gene by LipT(A) was selective with the human xenograft being most heavily stained.

EXAMPLE 7

Expression of Exogenous Wild-type p53 Protein in LipF (A)-p53 and LipT (A)-p53 Transfected JSQ-3 Cells This example demonstrates the expression of an exogenous gene, in this particular example wild-type p53, in cells being contacted and transfected by the delivery system of the invention. Having optimized the transfection efficiency both in vitro and in vivo, LipF(A) or LipT(A) was complexed to p53 expression plasmid pCMVp53, which contains 1.7 Kb cDNA of wt human p53 LipF(A)-p53) or (LipT(A)-p53). For DNA-dose response of p53 gene expression, $2 \times 10^5$ JSQ-3 cells were plated in each well of a 6-well plate. After 24 hours, cells were washed once with EMEM without serum and antibiotics, transfected with 1 ml transfection solution containing LipF(A)-p53 with increasing amounts (0.25–8 μg/$10^5$ cells) of pCMVp53 plasmid DNA complexed with LipF(A) or, as control, LipF(A)-pRo. Alternatively, the cells were transfected with LipT(A)-p53 or LipT(A)-pRo containing up to 4 μg plasmid DNA/$2 \times 10^5$ cells at the ratio of 1 μg DNA/10 nmol liposome/15 μg Tf in EMEM. Five hours after transfection, 1 ml EMEM supplemented with 20% FBS and 1 1 μg/ml hydrocortisone were added and cultured for another 48 hours The transfected cells were collected and lysed in RIPA buffer (Santa Cruz Biotechnology, Inc) and Western blot analysis was performed with the pantropic anti-p53 monoclonal antibody Ab-2 (Santa Cruz Biotechnology, Inc.) using standard procedures familiar to those skilled in the art. 40 μg of total protein was loaded per lane.

For a time-course of p53 gene expression, $2 \times 10^5$ JSQ-3 cells were transfected with 2 μg pCMVp53 or pCMVpRo complexed with LipT(A). The cells were collected every 24 hours up to 5 days after transfection and used for Western blot analysis.

To investigate the radiation effect on p53 gene expression, JSQ-3 cells were transfected with LipT(A)-p53 or LipT(A)-pRo (2 μg DNA/$2 \times 10^5$ cells) for 2 days, then trypsinized and irradiated at graded doses up to 6 Gy of $^{137}$Cs g-rays in a J. L. Shepard and Associates Mark I irradiator. The irradiated cells were replated and cultured for further 2 and 4 days before collecting for Western blot analysis.

After transfection into JSQ-3 cells in vitro, western blot analysis demonstrated that transfection with LipF(A)-p53 resulted in DNA-dose and time dependent expression of exogenous wtp53. To serve as control, LipF(A) was also complexed to plasmid pCMVpRo which carries wt p53 in the reverse orientation (LipF(A)-pRo). P53 expression in LipF(A)-pRo transfected JSQ-3 cells was the same as in the untransfected cells. Wtp53 expression was evident at 24 hr after LipF(A)-p53 transfection, peaking at 48 hr and becoming negligible by 120-hr post-transfection, again demonstrating the transient nature of this gene delivery system. This transitory expression is advantageous as it allows for repeated injections without accumulation of wtp53.

Western blot analysis was employed to demonstrate that the LipT(A)-transduced wtp53 was being expressed in JSQ-3 cells. Transfection with increased doses of p53-expression plasmid pCMVp53 complexed with LipT(A) (LipT(A)-p53) resulted in a DNA-dose dependent wtp53 expression, while no exogenous p53 expression was evident in JSQ-3 cells transfected with LipT(A)-pRo, which carries the wtp53 cDNA in reverse orientation under the CMV promoter. Wtp53 expression started from 24 hr after LipT(A)-p53 transfection and peaked on the second day, then reduced. Only traces of exogenous p53 were left 5 days after transfection, indicating that LipT(A)-mediated wtp53 expression was transient.

When the JSQ-3 cells were irradiated at 48 hr after LipT(A)-p53 or LipF(A)-p53 transfection (the peak of wtp53 expression), the exogenous wtp53 expression was substantially increased in accordance with the gamma-irradiation doses and was stable for up to 4 days, i. e., 6 days after transfection. These results demonstrated that gamma-irradiation can enhance and/or stabilize the exogenous wtp53, suggesting that the exogenous p53 is behaving in a way analogous to normal, endogenous wtp53, which is known to be stabilized by radiation exposure.

EXAMPLE 8

Sensitization of JSQ-3 to Radiation In Vitro

The presence of a mutated form of p53 has been shown to correlate with increased radiation resistance in some human tumors and cell lines (8, 10). Therefore, this example examined the effect of replacement of wtp53 by LipF(A)-mediated transfection on radiation survival. LipF(A)-mediated p53 transfection was able to sensitize JSQ-3 cells to radiation in a DNA dose-dependent manner. At the optimal transfection conditions, i.e., 3 μg plasmid DNA per $10^5$ cells, the $D_{10}$ value was substantially reduced from the highly resistant level found in the untransfected cells (6.65±0.43 Gy) to 4.33±0.06 Gy (p <0.01). This represents approximately a 6–10 fold sensitization to radiation killing. A $D_{10}$ value of 4.33 Gy (4 μg/$10^5$ cells) is similar to that of a radiosensitive human fibroblast cell line H500 ($D_{10}$=4.50±0.05 Gy) and in the range considered to be radiosensitive. Neither the pCMVp53 plasmid alone, nor the LipF(A)-pRo, had a substantial sensitizing effect, based upon the $D_{10}$ values (p>0.05) (FIG. 5). In terms of survival, this decrease of more than 2 Gy represents a dramatic increase in sensitivity to the killing effects of ionizing radiation. Clinically, this shift in sensitivity may render a resistant tumor curable by conventional radiation doses.

EXAMPLE 9

Apoptosis Induced by p53 Transfection and Gamma-irradiation

This example demonstrated that the reintroduction of wtp53 using the optimized transferrin-liposome complex of the invention was able to restore a functional p53 dependent apoptotic pathway. JSQ-3 cells were transfected with LipT (A)-p53 or LipT(A)-pRo (1 to 3 μg DNA/2×10$^5$ cells) and both the attached and floating cells were collected every day for 3 days for analysis of the percent of apoptotic cells. For radiation-induced apoptosis, the cells were transfected for 2 days, then trypsinized and irradiated as described above in Example 8. The replated cells were collected 4 days later for analysis of the percent of apoptotic cells. The collected cells were stained with the Annexin V-FITC Kit (Trevigen, Inc., Gaithersburg, Md.) according to the manufacturer's protocol. Annexin V-FITC binds specifically to phosphatidylserine present on apoptotic cells. The stained cells were analyzed using a FACStar cytometer (Becton & Dickinson).

To examine the effect of wtp53 restoration on the induction of apoptosis, JSQ-3 cells were transfected with LipT (A)-p53 or LipT(A)-pRo. A clear induction of apoptosis was observed in LipT(A)-mediated wtp53 restoration, in a dose-dependent manner. The percentage of apoptotic cells peaked on the second day of transfection which correlated with the levels of wtp53 expression in the cells as revealed by Western blot. To examine the effect of irradiation on the induction of apoptosis, the transfected cells were treated with different doses of gamma-irradiation. 2 to 4 days later, the cells were stained with Annexin V-FITC and analyzed by flow cytometry using FACStar (Becton & Dickinson). Gamma-irradiation induced substantial increase in the percent of apoptotic cells only in LipT(A)-p53 transfected cells, from 18.7% (0 Gy) to 38.7% (4 Gy) and 46.4% (6 Gy) 4 days after irradiation. No increase was observed in the untransfected (UT) cells and LipT(A) alone or LipT(A)-pRo treated cells. The increase was radiation dose-dependent and correlated with the wtp53 expression levels found in the Western blot data, demonstrating that the radiation enhancement of apoptosis was proportional to the wtp53 level in cells. That is, the more wtp53 that was expressed, the more apoptosis was induced.

EXAMPLE 10

Sensitization of JSQ-3 Xenograft Tumors to Radiation by the Systemic Delivery of LipF(A)-p53

In this example, the use of the systemically delivered folate-liposome-therapeutic molecule as a method of cancer treatment was demonstrated. In this particular example, the therapeutic molecule is the normal human wild-type p53 gene (pCMVp53).

Squamous cell carcinoma of the upper aerodigestive tract results in significant morbidity and mortality despite recent improvements in therapy Patients who present with early-stage disease (stage I or II) are generally treated with either surgery or radiation therapy, while the more common patients with advanced disease (stage III or IV) are generally treated with surgery followed by radiation. Despite this, half or more of patients treated for advanced stage disease will relapse at the site of original disease or with distant metastases and ultimately die. Presumably, a significant portion of these clinical failures result from radiation resistance in a subset of tumor cells. Therefore, the development of an effective method for sensitizing head and neck tumors to radiotherapy should have a profound effect on the treatment of this disease.

Mutant (mt) forms of the tumor suppressor gene p53 have been associated in a number of studies with poor clinical prognosis for various types of malignancy. P53 may also be involved in the development and progression of squamous cell carcinoma of the head and neck (SCCHN). By using a variety of detection methods, abnormalities in the p53 gene and/or its expression have been identified in 33%–100% of SCCHN tissues. The presence of mt p53 may also be indicative in SCCHN of increased frequency and more rapid recurrence of the tumor. Wild-type (wt) p53 has been shown to function in the regulation of the cell cycle after DNA damage or stress rather than during normal proliferation and development. Since the presence of mt p53 has also been found to correlate with increased radiation resistance (RR) in some human tumors and cell lines, and because a high percentage of head and neck tumors fail radiation therapy, it is conceivable that there is a cause-and-effect relationship between the lack of functional wtp53 found in a large number of SCCHN and this observed RR. The replacement of wtp53 may, therefore, result in the sensitization of these tumors to conventional radiotherapy.

2.5×10$^6$ JSQ-3 cells were injected subcutaneously on the lower back above the tail of 4–6 week old female athymic nude mice (NCr nu/nu). When the tumors reached the appropriate size, i.v. injection of LipF(A)-p53, pCMVp53 or LipF(A)-pRo, at 8 μg DNA/400 μl 5% dextrose/mouse, were given twice weekly for a total of 5 injections. 48 hours after the initial i.v. injection, the animals were secured in a lead holder which permitted only the tumor area to be irradiated, and the first fractionated dose of 2.5 Gy of $^{137}$Cs ionizing radiation administered. Thereafter, the animals were given 2.5 Gy every 48 hours to a total dose of 25 Gy. For comparison, a group of untransfected, as well as a group of mice receiving LipF(A)-p53, received no radiation.

Athymic nude mice bearing subcutaneous JSQ-3 tumors of approximately 25–40 mm$^3$ were intravenously injected, via the tail vein, with LipF(A)-p53 twice weekly (a total of 5 injections) and the tumor area only exposed to fractionated doses of gamma radiation (a total of 25 Gy). To determine if the transfected p53 protein was expressed in the tumors, one tumor from the untransfected, LipF(A)-p53 and LipF (A)-pRo groups was resected during the course of the experiment (after 3 injections and 12.5 Gy). A high level of exogenous p53 protein was manifest in the LipF(A)-p53 treated tumor, confirming that the folate-cationic liposome complex was able to deliver systemically the wtp53 gene to the tumors. Treatment with radiation alone had only a limited effect on the tumors in the untransfected animals. I.V. injection of pCMVp53 plasmid DNA, or LipF(A)-pRo, in combination with ionizing radiation, initially induced some inhibition of tumor growth. However, analogous to clinical circumstances, these tumors, like those in the untransfected animals, begin to re-grow after cessation of the radiation treatment. Although treatment with LipF(A)-p53 alone was able to inhibit tumor growth for a period of time during and even after the end of the i.v. infections, these tumors also began to increase in size within two weeks of the last i.v. injection. In contrast, 75% of the tumors which received the combination of LipF(A)-p53 plus radiation regressed completely, showing no signs of reoccurrence even 130 days post-radiation treatment. Moreover, the other 25% displayed only minimal residual tumor, which was static at less than 10% of the original tumor volume over the course of the experiment. Histologic examination of this residual mass showed that it represents mature scar with no proliferative tumor cells present.

Currently, after more than one year after cessation of treatment, the control animals have all either died or been humanely euthanized due to tumor burden. However, there is still no sign of tumor regrowth in animals that received the combination treatment.

Similar results were obtained from another, independent experiment, in which the initial tumor volumes were between 25 and 60 mm$^3$. Here again, approximately one year post-irradiation, no tumor regrowth is evident in the animals which received the combination treatment.

This is the first demonstration of total tumor regression mediated by a systemically delivered liposome-p53 complex. These in vivo studies demonstrated that the combination of systemic LipF(A)-p53 gene therapy and conventional radiotherapy was markedly more effective than either treatment alone.

EXAMPLE 11

Sensitization of JSQ-3 Xenograft Tumors to Radiation by the Systemic Delivery of LipT(A)-p53

In this example we demonstrate the use of the systemically delivered transferrin-liposome-therapeutic molecule as a method of cancer treatment. In this particular example, the therapeutic molecule is the normal human wild-type p53 gene (pCMVp53).

$2.5 \times 10^6$ JSQ-3 cells were injected subcutaneously on the lower back above the tail of 4–6 week old female athymic nude mice (NCr nu/nu). 7–10 days later, the tumors grew to approximately 40–50 mm$^3$ at the injection site. Freshly prepared LipT(A)-p53 or LipT(A)-pRo containing 8 $\mu$g DNA in 300 ml 5% dextrose were intravenously injected per mouse, via tail vein twice per week, for a total of 5 injections. 48 hours after the initial i.v. injection, the animals were secured in a lead restraint so that only the tumor area was exposed to gamma-irradiation, and the first fractionated dose of 2.5 Gy of $^{137}$Cs ionizing radiation administered. Thereafter, the animals were given 2.5 Gy every 48 hours to a total dose of 25 Gy. For comparison, a group of untransfected, as well as a group of mice with LipT(A)-p53 injection receiving no radiation were used as controls. The tumor sizes were measured weekly in a blinded manner.

Two independent experiments with SCCHN (JSQ-3) xenograft tumors were been performed with similar results. In the first, mice bearing subcutaneous JSQ-3 tumors of approximately 25–40 mm$^3$ were injected, via the tail vein, with LipT(A)-p53 twice weekly (a total of 5 injections) and only the tumor area exposed to fractionated doses of gamma radiation (a total of 25 Gy). Short-term radiation effects on tumor growth were evident in cells transfected using the control LipT(A)-CMVpRo. There was only minimal tumor growth inhibition in the animals that received the LipT(A)-CMVp53 without radiation. In contrast, all of the tumors that received the combination of LipT(A)-CMVp53 plus radiation exhibited virtually complete regression, showing no signs of reoccurrence even 153 days post-radiation treatment. By this time, the tumor-bearing animals in control groups had died or were humanely euthanized due to excessive tumor burden. However, at one year post-irradiation the combination treatment group (p53 and radiation) still showed no sign of tumor regrowth. As in the case of animals treated with the combination of LipF(A)-p53 and radiation, by one month post-treatment, only scar tissue and a few invading Langerhan's cells were present in the residual tissue at the site of the original tumor in an animal that received the combination treatment. Similar results were observed in a second in vivo experiment.

EXAMPLE 12

Effect of the Combination Therapy in a Second Cancer Model

This example illustrates that the efficacy of this novel combination of liposome-mediated, tumor-targeted p53 gene therapy and conventional radiotherapy is not limited to SCCHN, thereby increasing the clinical relevance of this system. The effect of the combination of folate-targeted, liposome-mediated p53 gene therapy and radiation on human prostate cell line DU145 in vivo was evaluated. This adenocarcinoma cell line was originally derived from a lesion in the brain of a patient with widespread metastatic carcinoma of the prostate and is reported to carry mtp53. We have found this cell line to be resistant to gamma-radiation killing ($D_{10}$=5.8±0.22 Gy), one of the primary forms of adjuvant therapy for this disease. Earlier in vitro experiments suggested that replacing the neutral lipid DOPE with cholesterol may result in increased transfection efficiency in this distinct tumor cell type. Based upon the luciferase activity, we found that LipF(D) gave more than a four-fold increase in transfection efficiency as compared to LipF(A) in DU145 cells. Therefore, mice bearing DU145 tumors of approximately 70 mm$^3$ were i.v. injected via the tail vein with LipF(D)-p53 approximately every 5 days (a total of 5 injections) and the tumors exposed to fractionated doses of gamma-irradiation (a total of 25 Gy). In this experiment, a non-folate targeted liposome-p53 composition (Lip(D)-p53) was also used as a control. The results with these prostate tumors were quite similar to those of the SCCHN tumors. Radiation alone, LipF(D)-pRo plus radiation, and non-targeted Lip(D)-p53 plus radiation had some inhibitory effect on tumor growth during the course of the treatments. However, these tumors all rapidly increased in size once treatment ceased. In contrast, the combination of LipF(D)-p53 plus radiation again resulted in long-term regression of the tumors even at day 84 which is 64 days post-treatment. An observed drop in tumor volume of the control group at Day 63 was due to loss of animals in this group due to tumor burden. A second experiment with tumors of approximately 100 mm$^3$ showed analogous results with no regrowth observed even 47 days after all treatment had ceased.

EXAMPLE 13 chemosensitization of JSQ-3 to Cisplatin (CDDP) In Vitro

In addition to radiation, chemotherapy is becoming more commonly used in the treatment of SCCHN. As lack of functional wtp53 has been associated with failure to respond to chemotherapy, in this example we examined the effect of ligand-facilitated liposome mediated wtp53 gene therapy on sensitization of SCCHN cell line JSQ-3 to chemotherapeutic agents. $1 \times 10^4$ cells were plated/well of a 96-well plate. 24 hours later, the cells were transfected with LipT(A)-p53. Two days after transfection, anti-neoplastic agents were added at increasing concentrations (in triplicate). 4–6 days later the XTT cell proliferation assay was performed and $IC_{50}$ values, the drug concentration yielding 50% growth inhibition, calculated. Treatment with as little as 0.2 $\mu$g of wtp53 DNA complexed to LipT(A) was shown to substantially sensitize JSQ-3 cells to both CDDP and 5-FU, two drugs frequency employed in adjuvant chemotherapy. While transfection with the LipT(A) complex alone, or LipT(A) carrying wtp53 in the reverse orientation (LipT(A)-pRo) yielded some sensitization to CDDP, a 24 fold level of sensitization over that of the untransfected cells was evident in the LipT(A)-p53 transduced cells. Furthermore, a 15.4 fold sensitization of JSQ-3 to the chemotherapeutic agent 5-FU was also observed after transfection with the LipT(A)-p53 complex.

EXAMPLE 14

P53-mediated Chemosensitization as Indicated by Enhanced Induction of Apoptosis

This example examines the effect of ligand-liposome mediated wtp53 restoration on chemotherapeutic agent induced apoptosis. JSQ-3 cells were seeded in 6-well plates and transfected with LipT(A)-p53, LipT(A)-pVec (the vector without the p53 gene) or LipT(A) alone, at 1 or 2 ug DNA per $2\times10^5$ cells. 24hr later, chemotherapeutic agents were added to each set of plates, at concentrations near the $IC_{50}$ values for each cell line. After one additional day incubation, both the attached and floating cells were collected and stained with AnnexinV-FITC, which binds specifically to phosphatidylserine present on apoptotic cells, using an Annexin V-FITC Kit (Trevigen, Inc., Gaithersgurg, Md.) according to the manufacturer's protocol. The stained cells were analyzed on FACStar flow cytometer (Becton and Dickinson).

A p53 DNA dose dependent induction of apoptosis was observed in the cells treated with the LipT-mediated wtp53 complex of the invention. Moreover, the addition of chemotherapeutic agents (CDDP, Taxotere, 5-FU) at doses near their $IC_{50}$ values induced a substantial increase in the percent of apoptotic cells in the population only in LipT (A)-p53 transfected cells, not in the untransfected (UT) and LipT(A) only or LipT(A)-pVec transfected cells. The increase was p53 DNA dose-dependent and correlated with the wtp53 expression levels observed on Western blots, demonstrating that the chemotherapeutic agents induced enhancement of apoptosis was proportional to the wtp53 level in cells, i.e., the more wtp53 expressed, the more apoptoses was induced. The increase in apoptosis observed after the combination of the LipT(A)-p53 plus drug was substantially more than the sum of the chemotherapeutic agent alone (UT plus drug) plus p53 transfection alone (p53 no drug), indicating a synergistic effect when p53 gene therapy was combined with chemotherapeutic agents.

EXAMPLE 15

Chemosensitization of MDA-MB-435 to Cisplatin or Doxorubicin In Vitro by Ligand-liposome-p53

In the treatment of breast cancer, the failure of a substantial portion of tumors, and their metastases, to respond to adjuvant chemotherapy is a major concern. In this example we examined the ability of the delivery system of the invention to sensitize breast cancer cells to currently used chemotherapeutic agents.

Human breast cancer cell line MDA-MB-435 was employed. The ligand-liposome complex used was the composition, which had been optimized for head and neck squamous cells—a different histological cell type from that found in breast cancer. Transfection with LipT(A)-p53 increased the effect of doxorubicin on MDA-MB-435 cells by four fold and the effect of CDDP by almost 12 fold, as compared to the untransfected cells. As seen with the SCCHN cells, there was also some sensitization by the LipT(A)-pRo complex. Here again, although not yet optimized for mammary carcinomas, chemosensitization of breast cancer cells by transfection with LipT(A)-p53 was demonstrated.

Even more striking results were obtained using a composition, LipF(C), tailored for adenocarcinoma, the histological cell type of most breast cancers. As above, the $IC_{50}$ values were determined by the XTT assay. Transfection with LipF(C)-p53 increased the effect of doxorubicin on MDA-MB-435 cells by 73.6-fold and the effect of Taxol by 31.6-fold, as compared to the untransfected cells. As seen with the SCCHN cells, there was also some sensitization by the LipF(C)-pRo complex. These results demonstrate chemosensitization of breast cancer cells by transfection with transferrin- and folate-targeted liposome-p53 complex.

EXAMPLE 16

Chemosensitization of Breast Cancer Cells by LipF-p53 Gene Therapy In Vivo

This example shows the ability of the systemically delivered ligand-liposome-therapeutic molecule complex of the invention to be an effective therapeutic agent against cancer cells in vivo. Mice bearing subcutaneous mammary fat pad MDA-MB-435 tumors of approximately 100 $mm^3$ were i.v. injected via the tail vein with LipF(C)-p53 every 3–4 days for a total of eight injections. Doxorubicin (Dxr) (10 mg/kg) was injected i.v. weekly for 4 weeks. The combination of LipF(C)-p53 and Dxr substantially inhibited the growth of the tumors. In a second experiment, two separate liposome compositions [LipF(E) and LipF(C)] were employed. Both demonstrated an effect in combination with Dxr, with the LipF(C)-p53 composition being superior to that of LipF(E)-p53.

EXAMPLE 17

Optimization of Ligand-liposome Transfection in Different Cancer Cell Lines

In this example we further explored the ligand-cationic liposome system, preparing a panel of ligand-targeted cationic liposomes to optimize the transfection efficiency to a variety of human and rodent cancer cells.

Cationic liposomes were prepared as follows:

| | |
|---|---|
| LipA DOTAP/DOPE | 1:1 molar ratio |
| LipB DDAB/DOPE | 1:1 molar ratio |
| LipC DDAB/DOPE | 1:2 molar ratio |
| LipD DOTAP/Chol | 1:1 molar ratio |
| LipE DDAB/Chol | 1:1 molar ratio |
| LipG DOTAP/DOPE/Chol | 2:1:1 molar ratio |
| LipH DDAB/DOPE/Chol | 2:1:1 molar ratio |

1. Folate series: Each of the above formulations plus 1%–5% folate-DOPE or folate-DSPE.
2. Transferrin series: Each of the above formulations mixed with holo-transferrin in medium or buffer, then mixed with reporter gene plasmid DNA in medium or buffer to form the complex.

The firefly luciferase gene in plasmid pCMVLuc or *E. coli* β-galactosidase gene in plasmid pCMVb was used as a reporter gene.

Preparation of DNA-liposame Complexes:

The various DNA-Liposome-Folate complexes was prepared by mixing, in polypropylene tubes, equal amounts of serum-free medium and the reporter gene plasmid DNA in TE buffer (10 mM Tris-HCl, 1 mM EDTA, pH 8.0), and equal amounts of serum-free medium with the folate-liposome (LipA-F, LipB-F, LipC-F, LipD-F, LipE-F, tipG-F, LipH-F) in sterile water (2 μmol/ml total lipids). After 10–15 min at room temperature, the two solutions were mixed together and incubated 15–30 min at room temperature with frequent rocking. The DNA to lipid ratios in optimization ranged from 1:0.1 to 1:50 ug/nmol.

The various DNA-Liposome-Transferrin complexes were prepared by the addition of Tf (iron-saturated, Sigma, 4–5 mg/ml in water, filtered with 0.22 mm filter) to serum-free medium. 5–15 min later, cationic liposome (LipA, LipB, LipC, LipD, LipE, LipG, LipH) was added and mixed. After 5–15 min. incubation at room temperature with frequent rocking, an equal amount of medium containing reporter gene plasmid DNA was added and mixed, and incubated 15–30 min at room temperature with frequent rocking. The DNA/Lipid/Tf ratios in optimization were in the range of 1/(0.1–50)/(0.1–100) μg/nmol/μg.

Cell lines:

Optimization was performed on the following cell lines:

Human squamous cell carcinoma of head and neck: JSQ-3, HN17B, HN22a, HN-38, SCC-25.

Human breast cancer: MDA-MB-231, MDA-MB-435, MDA-MB-453, MCF-7.

Human prostate cancer: DU145, LNCaP, Ln-30, P4–20.

Human ovary cancer: SKOV-3, PA-1

Human pancreatic cancer: PANC-1

Human colon cancer: SW480, LS174T, SK-CO-1

Human glioblastoma: U-87

Human cervical cancer: HTB-34, ME180

Human lung cancer: CALU-3

Human gastric cancer: Hs 746T

Human liposarcoma: SW 872

Human melanoma: SK-MEL-31

Human choriocarcinoma: JEG-3

Human rhabdomyosarcoma: Hs 729T

Human retinoblastoma: Y79

Human normal breast epithelial: Hs578Bst

Human endothelial: HUV-EC-C

Mouse melanoma: B16/F10

Rat prostate cancer: PA-III, AT.61

Rat brain cancer: RT-2

Optimization by Luciferase Assay:

$5 \times 10^4$ cells/well were plated in a 24-well plate. 24 hours later, the cells were washed once with medium without serum, 0.3 ml medium without serum and antibiotics was added to each well. The freshly prepared LipT-pCMVLuc or LipF-pCMVLuc complexes containing different amounts of plasmid DNA (up to 1.0 μg in 0.2 ml) medium was added to the cells. After a 5-hour incubation at 37° C. and 5% $CO_2$, 0.5 ml medium supplemented with 20% fetal bovine serum was added to each well. 24 hours later, the cells were washed once with PBS, lysed with 100 μl/well 1X Reporter Lysis Buffer (Promega), and the expressed luciferase activities were measured with Luciferase Assay System (Promega) on a Luminometer. The protein concentration of the cell lysate was measured using the Bio-Rad DC Protein Assay Kit (Bio-Rad Laboratories). The results were expressed as relative light unit (RLU) per ug of total protein.

Optimization by β-Galactosldase Calorimetric Assay:

$1 \times 10^4$ cells were plated in each well of a 96-well plate or $5 \times 10^4$ cells/well in 24-well plate. 24 hours later, the cells were washed once with medium without serum or antibiotics and 100 μl transfection solution containing various Amounts of LipT-pCMVb, LipF-pCMVb, or pCMVb alone, were added to each well. After 5 hours at 37° C., an equal amount of medium containing 20% fetal bovine serum was added to each well. 48 hours later, the cells were washed once with PBS, and lysed in 1X reporter lysis buffer (Promega). The cell lysates were treated with 100 μl 150 μM 0-nitrophenyl-β-galactopyranoside in 20 mM Tris (pH 7.5) containing 1mM $MgCl_2$ and 450 μM β-mercaptoethanol at 37° C. for 0.5 hour. The reaction was stopped by the addition of 150 μl/well of 1 M $Na_2CO_3$. The absorbency was determined at 405 nm. Purified β-galactosidase (Boehringer) was used as standard. The results were expressed as milli-unit of β-galactosidase equivalent per ug of total protein.

Histochemical Staining:

For histochemical studies of ligand-liposome-pCMVb transfection, cells at 60% confluence (in a 24-well plate) were transfected for 5 hours as described above. After an additional 2 days in culture, the cells were fixed and stained with X-gal. Transfection efficiency was calculated as percentage of blue-stained cells.

Transfection Efficiencies of the Different Liposome Compositions with Different Cell Lines:

As shown in Table 2, LipT(A) and LipT(D) demonstrated the highest transfection efficiency for JSQ-3 cells, 3–8 fold more efficient than other liposome formulations. LipT(D) was the most efficient for both MDA-MB-435 and DU145. At the ratio of 1/12/15 (DNA μg/Lip nmol/Tf μg) or higher, LipT(D) gave high efficiency to JSQ-3 and LipT(A) to MDA-MB-435 cells, but cytotoxicity became obvious. More importantly, when preparing Tf-Lip-DNA complexes for in vivo experiments, the complex at this ratio or higher (lipids) tends to precipitate, the solution of the complex tends to become cloudy (i.e., not as clear as solutions prepared at lower ratios) and not stable. Therefore, the preferred ratio of LipT is 1/10/12.5 (DNA μg/Lip nmol/Tf μg).

TABLE 2

| Liposomes | Ratio** | DU145 | MDA-MB-435 | JSQ-3 |
|---|---|---|---|---|
| LipT(A) | 1/6/7.5 | 0.62 | 1.18 | 24.62 |
| | 1/8/10 | 1.54 | 2.90 | 76.07 |
| | 1/10//12.5 | 3.05 | 2.32 | 117.64 |
| | 1/12/15 | 1.50 | 14.56 | 81.09 |
| LipT(B) | 1/6/7.5 | 1.06 | 6.35 | 44.11 |
| | 1/8/10 | 0.97 | 5.91 | 36.45 |
| | 1/10/12.5 | 0.78 | N/A | 43.00 |
| | 1/12/15 | 0.28 | 5.90 | 38.98 |
| LipT(C) | 1/6/7.5 | 0.043 | 0.66 | 2.80 |
| | 1/8/10 | 0.087 | 1.63 | 7.35 |
| | 1/10/12.5 | 0.33 | 2.59 | 16.59 |
| | 11/12/15 | 0.25 | 3.48 | 17.29 |
| LipT(D) | 1/6/75 | 0.076 | 4.00 | 1.88 |
| | 1/8/10 | 0.26 | 7.43 | 3.43 |
| | 1/10/12.5 | 0.92 | 9.63 | 42.20 |
| | 1/12/15 | 3.06 | 13.44 | 124.60 |
| LipT(E) | 1/6/7.5 | 0.54 | 7.56 | 9.46 |
| | 1/8/10 | 0.87 | 5.31 | 8.96 |
| | 1/10/12.5 | 1.12 | 4.52 | 20.91 |
| | 1/12/15 | 1.33 | 6.21 | 27.95 |
| Plasmid Alone | | 0.0001 | 0.0034 | 0.0001 |

*$\times 10^6$ RLU/mg protein
**Ratios of DNA μg/Lip nmol/Tf μg

Similar to transferrin, LipF(A) and LipF(C) provided the best results for JSQ-3 cells, 2 to 8-fold more efficient than other liposome formulations (Table 3). Interestingly, folate-liposomes give totally different patterns of efficiencies compared with Tf-liposomes in both MDA-MB-435 and DU145 cells, and in other cell lines as well. LipF(C) provided the best results for MDA-MB-435 and LipF(E) provided the best results for DU145 (Table 3). Similar results with less efficiency were obtained in some cancer cell lines transfected with

TABLE 3

| Liposomes | | DU145 0.25 ug DNA | DUI145 0.5 ug DNA | MDA-MB-435 0.5 ug DNA | JSQ-3 0.5 ug DNA |
|---|---|---|---|---|---|
| LipF(A) | 1/6** | 0.05 | | | |
| | 1/8 | 0.31 | 0.58 | 2.16 | 76.90 |
| | 1/10 | 0.16 | 0.29 | 0.59 | 77.96 |
| | 1/12 | 0.18 | | | |

TABLE 3-continued

| Liposomes | | DU145 0.25 ug DNA | DUI145 0.5 ug DNA | MDA-MB-435 0.5 ug DNA | JSQ-3 0.5 ug DNA |
|---|---|---|---|---|---|
| LipF(B) | 1/6 | 0.42 | | | |
| | 1/8 | 1.27 | 2.68 | 2.26 | 44.80 |
| | 1/10 | 1.03 | 1.94 | 1.71 | 42.15 |
| | 1/12 | 1.61 | | | |
| LipF(C) | 1/6 | 0.10 | | | |
| | 1/8 | 0.44 | 1.14 | 3.58 | 36.27 |
| | 1/10 | 0.54 | 1.15 | 1.62 | 83.88 |
| | 1/12 | 0.35 | | | |
| LipF(D) | 1/6 | 0.05 | | | |
| | 1/8 | 0.05 | 0.53 | 1.07 | 25.95 |
| | 1/10 | 0.38 | 0.74 | 0.64 | 34.47 |
| | 1/12 | 0.20 | | | |
| LipF(E) | 1/6 | 2.71 | | | |
| | 1/8 | 2.08 | 2.23 | 0.98 | 12.12 |
| | 1/10 | 1.63 | 2.95 | 1.07 | 23.91 |
| | 1/12 | 1.60 | | | |
| Plasmid | | $0.27 \times 10^{-6}$ | $0.13 \times 10^{-3}$ | 0 | 0 |

*$\times 10^6$ RLU/mg protein
**Ratios: DNA $\mu$g/Lip nmol

Table 4 shows the preferred ligand-liposome formulations for some of the cell lines we have tested in vitro using the ligand-liposome system disclosed in the invention. It should be noted that the optimal compositions for in vitro transfection are not is necessarily the optimal ones for in vivo transfection. But it tends to be that the in vitro preferred compositions are a good starting point leading to the preferred compositions for in vivo. Therefore, in vivo optimization using nude mouse xenograft models is necessary before the in vivo systemic gene therapy experiments, as disclosed in the invention.

TABLE 4

| Cell Line | Tf-liposome | Folate-liposome |
|---|---|---|
| JSQ-3 | LipT(A),(D) | LipF(A),(C) |
| HN 17B | LipT(B) | |
| HN 22a | LipT(A) | |
| HN 38 | LipT(B) | |
| SCC-25 | LipT(A) | |
| SCC-25cp | LipT(A) | |
| MDA-MB-231 | LipT(E) | |
| MDA-MB-435 | LipT(D),(A) | LipF(C),(B) |
| MDA-MB-453 | LipT(C) | |
| DU 145 | LipT(D),(H) | LipF(E) |
| P4-20 | LipT(A) | |
| SKOV-3 | LipT(D),(B) | |
| PA-1 | LipT(A) | |
| PANC-1 | LipT(D),(H) | LipF(D),(A) |
| SW 480 | LipT(A) | |
| LS 174T | | LipF(D) |

TABLE 4-continued

| Cell Line | Tf-liposome | Folate-liposome |
|---|---|---|
| SK-CO-1 | | LipF(E) |
| U-87 | LipT(D),(A) | |
| HTB-34 | LipT(C),(A) | LipF(C) |
| ME 180 | | LipF(E) |
| CALU-3 | | LipF(D) |
| HS 746T | | LipF(E) |
| HS 578 Bst | | LipF(E) |
| HUV-EC-C | | LipF(E) |
| B16 F10 | LipT(A),(C) | LipF(E) |
| JEG-3 | | LipF(B) |
| HS 729T | | LipF(B) |
| Y79 | | LipF(D) |
| PA-III | | LipF(C),(H) |
| AT6.1 | LipT(H) | LipF(H) |
| RT-2 | | LipF(B) |

Effect of Serum on the Transfection Efficiency of Ligand-liposomes:

LipT(D) had the highest level of transfection efficiency with human glioblastoma cell line U-87 without serum. However, in the presence of 10% serum its transfection efficiency was substantially reduced, while LipT(A) was most efficient in the presence of serum for this cell line. For human pancreatic cancer cell line PANC-1, serum appeared to enhance the transfection with some liposome compositions, with LipT(H) displaying the highest level of efficiency. Here again, we observed different transfection efficiency patterns in different cell lines, and different effects of serum on transfection efficiency. For the purpose of in vivo transfection, serum effects should be considered during optimization.

EXAMPLE 18

Chemosensitization of Other Cell Lines by Tf- or Folate-Liposome-Mediated Wtp53 Gene Therapy In Vitro This example summarizes part of the in vitro p53-mediated chemosensitization experiments (XTT assays) performed on the cell lines for which transfection with transferrin-coupled or folate-coupled liposomes is described in Example 17. The data presented in the following table demonstrate that both LipT- and LipF-mediated p53 gene transfection can sensitize these tumor cells to chemotherapeutic agents. The chemosensitization effect is dependent upon the liposome used and the p53 DNA dose. VIN= vinblastine; DXR=doxorubicin; CDDP=cisplatin. Fold Sensitization is calculated from the individual $IC_{50}$ values. DNA dose=ug of DNA applied per well (approximately $1 \times 10^4$ cells/well in a 96-well plate).

| Cell line | Drug | Liposome | DNA Dose | IC50 p53 | Vector | Lip only | UT | Fold Sensitization p53 vs Vector | p53 vs UT |
|---|---|---|---|---|---|---|---|---|---|
| MDA-MB-231 | Vln | LipF(B) | 0.15 | 0.42 | 1.07 | 1.23 | 1.57 | 2.6 | 3.8 |
| | Vln | LipF(A) | 0.15 | 0.50 | 1.42 | 1.47 | 1.81 | 2.9 | 3.6 |
| | Vln | LipF(C) | 0.15 | 0.48 | 1.69 | 1.47 | 1.81 | 3.5 | 3.8 |
| | DXR | LipF(B) | 0.15 | 0.07 | 0.24 | 0.27 | 0.27 | 3.6 | 4.0 |
| | DXR | LipF(A) | 0.15 | 0.11 | 0.24 | 0.22 | 0.20 | 2.2 | 1.8 |
| | DXR | LipF(C) | 0.15 | 0.02 | 0.09 | 0.30 | 0.27 | 4.5 | 13.5 |
| | Taxol | LipF(C) | 0.12 | 2.90 | 11.70 | 11.70 | 54.10 | 4.0 | 18.7 |
| | Taxol | LipF(C) | 0.08 | 6.10 | 10.00 | 10.00 | 52.00 | 1.6 | 8.5 |
| | Taxol | LipT(C) | 0.12 | 14.70 | 46.70 | 10.00 | 52.00 | 3.2 | 3.5 |

-continued

| Cell line | Drug | Liposome | DNA Dose | p53 | IC50 Vector | Lip only | UT | Fold Sensitization p53 vs Vector | p53 vs UT |
|---|---|---|---|---|---|---|---|---|---|
| MDA-MB-435 | DXR | LipF(C) | 0.12 | 0.01 | 0.74 | 0.74 | 0.89 | 62.9 | 76.1 |
| | DXR | LipF(C) | 0.08 | 0.01 | 0.58 | 0.76 | 0.93 | 46.3 | 73.5 |
| | DXR | LipT(B) | 0.10 | 0.01 | 0.54 | 0.79 | 0.85 | 54.0 | 85.0 |
| | Taxol | LipF(C) | 0.12 | 1.12 | 10.79 | 34.15 | 39.80 | 9.6 | 35.5 |
| | Taxol | LipF(C) | 0.08 | 1.36 | 14.13 | 36.87 | 42.99 | 10.4 | 31.6 |
| | Taxotere | LipF(B) | 0.10 | 0.11 | 3.75 | 13.50 | 10.00 | 34.7 | 92.6 |
| | Taxotere | LipT(B) | 0.08 | 0.07 | 0.80 | 3.10 | 3.60 | 10.8 | 48.7 |
| JSQ-3 | Taxotere | LipF(A) | 0.10 | 0.29 | 1.73 | 2.13 | 2.53 | 6.0 | 8.7 |
| | Taxotere | LipF(C) | 0.10 | 1.36 | 3.98 | 3.40 | 13.59 | 2.9 | 10.0 |
| | Taxotere | LipF(C) | 0.08 | 0.79 | 3.98 | 3.40 | 13.59 | 5.0 | 17.2 |
| | Taxotere | LipF(B) | 0.10 | 0.86 | 1.85 | 13.59 | 14.68 | 2.2 | 17.1 |
| | Taxol | LipF(C) | 0.10 | 1.70 | 3.40 | 6.30 | 15.85 | 2.0 | 9.3 |
| | Taxol | LipF(C) | 0.08 | 1.47 | 3.40 | 6.30 | 15.85 | 2.3 | 10.8 |
| | Taxol | LipF(B) | 0.10 | 0.86 | 3.16 | 17.11 | 17.11 | 3.7 | 19.9 |
| DU145 | Taxotere | LiPF(C) | 0.10 | 0.86 | 6.60 | 1.35 | 41.97 | 7.7 | 48.8 |
| | Taxotere | LipF(C) | 0.08 | 0.32 | | | 41.97 | | 130.3 |
| | Taxotere | LipF(B) | 0.10 | 0.56 | 3.40 | 14.68 | 39.80 | 6.1 | 71.1 |
| | Taxol | LipF(C) | 0.10 | 0.71 | 4.20 | 4.80 | 13.20 | 5.9 | 18.6 |
| | Taxol | LipF(B) | 0.10 | 1.40 | 5.50 | 13.50 | 16.30 | 3.9 | 11.6 |
| PANC-1 | CDDP | LipF(B) | 0.10 | 5.05 | 13.33 | 14.86 | 18.43 | 2.6 | 3.6 |
| | Taxotere | LipF(A) | 0.15 | 1.63 | 10.36 | | 11.50 | 6.4 | 7.1 |
| | Taxotere | LipF(B) | 0.15 | 0.14 | 1.30 | 10.00 | 12.30 | 9.3 | 87.9 |
| | Taxotere | LipF(C) | 0.20 | 0.15 | 1.70 | 1.90 | 12.30 | 11.3 | 82.0 |
| | Gemzar | LipT(B) | 0.20 | 0.05 | 0.81 | | 0.80 | 16.2 | 15.1 |
| U87 | Gemzar | LipF(B) | 0.10 | 0.28 | 1.07 | 0.76 | 1.28 | 3.9 | 4.7 |
| | Gemzar | LipF(C) | 0.10 | 0.50 | 1.15 | 1.20 | 1.23 | 2.3 | 2.5 |
| | Gemzar | LipT(A) | 0.20 | 0.20 | 1.00 | 1.00 | 1.00 | 5.0 | 5.0 |

EXAMPLE 19

Effect of the Combination of Systemically Delivered LipF-p53 and Chemotherapy on the Growth of DU145 Xenografts In Vivo Chemotherapy is becoming more commonly used in the treatment of prostate cancer. Lack of functional wtp53 has been associated with failure to respond to chemotherapy. This example examines the effect of the combination of ligand-liposome-p53 and chemotherapeutics on the growth of prostate tumor xenografts in vivo.

Mice bearing subcutaneous DU145 xenograft tumors of approximately 100 mm$^3$ were injected, via the tail vein, with a ligand-liposome p53 complex using folate as the targeting ligand (LipF(B)-p53). This liposome complex was administered twice/week (to a total of 5 injections) along with the chemotherapeutic agent docetaxel at a dose of 10 mg/kg. Treatment of the animals with neither the LipF(B)-p53 complex alone, nor docetaxel alone had any substantial effect on tumor growth. However, treatment with the combination of the systemically delivered LipF(B)-p53 of the invention plus docetaxel led to substantial tumor regression. Though the complex used was not been completely optimized for prostate tumor cells, these findings strongly support the ability of systemically delivered, targeted-liposomes to deliver wtp53 to the tumors resulting in their sensitization to conventional therapeutics.

EXAMPLE 20

Effect of the Combination of Systemically Delivered LipF-p53 and Chemotherapy on the Growth of PANC-1 Xenografts In Vivo This example demonstrates the effect of the combination of ligand-liposome-p53 and chemotherapeutics on the growth of pancreatic cancer xenografts in vivo. Xenograft tumors of pancreatic cancer cell line PANC-1 were induced by the subcutaneous inoculation of greater than 1×10$^7$ cells onto athymic nude mice. When the tumors reached approximately 500–1000 mm$^3$, the tumors were excised and minced into small (<1 mm) pieces. These freshly prepared tumor pieces (suspended in PBS) were inoculated subcutaneously (using a 14 g needle) onto the flanks of athymic nude mice. When the tumors reached an average of 100 mm$^3$ in volume, treatment was begun. The animals received, via intravenous injection, LipF(B)-p53. This liposome complex was administered twice/week to a total of 7 injections. The chemotherapeutic agent gemcitabine was also administered intraperitoneally at a dose of either 60mg/kg or 120mg/kg twice weekly. A total of 13 gemcitabine injections were administered. One group of animals also received twice weekly intratumoral injections of LipF(B)-p53 (a total 6) in addition to the intravenous administration of the LipF(B)-p53 and gemcitabine. The control groups of animals that received no treatment, only gemcitabine, only LipF(B)-p53, or LipF(B) complexed to the pCMV vector without p53 (LipF(B)-Vec) were euthanized due to tumor burden by day 54. In contrast, the three groups of animals receiving the combination of LipF(B)-p53 and gemcitabine showed substantial growth inhibition of their tumors, even 12 days after the end of treatment. This was particularly evident in the group that received both i.v. and i.t injections. Therefore, once again, using another tumor model, the combination of systemically delivered ligand-liposome-therapeutic molecule and chemotherapeutic agent was found to be substantially more effective than currently available therapies.

EXAMPLE 21

Chemosensitization of Tumor Cells by Ligand-Targeted, Liposome-Mediated Antisense Oligonucleotides In Vitro and In Vivo This example demonstrates the ability of the systemically administered ligand-liposome-therapeutic molecule delivery system of the invention to deliver small oligonucleotides as the therapeutic molecule. Further, this example demonstrates the ability of the systemically administered, ligand-liposome-delivery of the small oligonucleotides to sensitize the contacted tumor cells to chemotherapeutic agents.

Optimization of the Folate-liposome (LipF) Composition for Various Tumor Cell Types:

Starting with the ligand-liposome complex derived for SCCHN cell lines and described above, further ligand-liposome compositions optimized for delivering anti-sense HER-2 (AS-HER-2) oligonucleotides to tumor cells were developed. The AS-HER-2 oligonucleotide was a 15-mer complementary to a sequence near the initiation codon of the HER-2 gene. (Pirollo et al., BBRC 230, 196–201 (1997)).

Saturation of Liposomes by Oligonucleotides:

Multiple new folate-liposomes (LipF) compositions were produced by varying the cationic and neutral lipid in the complex. Helper lipids were also included in some compositions. The ratio of cationic to neutral lipid was also varied. Using $^{32}$P-labled AS-HER-2 oligonucleotide, we determined the ratio of liposome to oligonucleotide that gave optimal binding of the oligonucleotide to the various compositions. An example of these studies is shown in the following table where a comparison is made between LipF compositions B and C versus Liposome A, which is the LipF composition optimized for SCCHN.

| Ratio Lip:Oligo | Liposome A | Liposome B | Liposome C |
| --- | --- | --- | --- |
| 1:10 | 23% | 51.6% | 44.25% |
| 1:1 | 87.7% | 77.9% | 61.97% |
| 5:1 | 90% | 90.7% | 72.6% |
| 10:1 | 93% | 98% | 86.7% |
| 25:1 | 100% | 100% | 100% |

There is clearly a difference in the oligonucleotide binding between the three compositions. Nevertheless, complete saturation is achieved with all three at a liposome:oligonucleotide ratio of 25:1. However, a substantial amount of toxicity was evident at this ratio. It is also evident from these data that for different liposome compositions, the optimal ratio is dramatically different.

AS-HER-2 Oligonucleotide Uptake by Tumor Cell Lines with Various LipF Compositions:

Transfection experiments were performed with the LipF compositions and human breast cancer cell line MDA-MB-435, SCCHN cell line JSQ-3, prostate tumor cell line DU145 and pancreatic tumor cell line PANC 1, to determine the transfection efficiency of each LipF composition. Those used were the four compositions (designated B-E) which were found to have the most efficient binding of the oligonucleotide. The two molar ratios of Liposome:Oligonucleotide used initially in these studies were 10:1 and 25:1, those found (see above) to possess the highest oligonucleotide binding levels. However, a ratio of 25:1 was found to be toxic to the cells. Therefore, the remainder of the experiments were performed using a ratio of 10:1 (liposome:oligonucleotide). Transfections, using $^{32}$P labeled AS-HER-2, were performed as previously described for LipF(A)-p53 for SCCHN. However, after twenty hours incubation at 37° C., the media was removed and the cells washed five times with PBS. The media and washes were combined and the amount of unincorporated label ascertained. The amount of cell associated $^{32}$P-labelled anti-HER-2 oligonucleotide was determined by comparing the $^{32}$P level within the cells versus the unincorporated oligonucleotide. In these studies LipF(A) is the composition originally optimized for SCCHN. As shown in the following table, LipF composition B yielded the highest level of transfection efficiency in MDA-MB-435 breast cancer cells, while LipF composition E was better for both DU145 and PANC I. Therefore, LipF composition B [LipF(B)] was used for the remainder of the studies with MDA-MB-435, described below.

| CELL LINE | Liposome A | Liposome B | Liposome C | Liposome D | Liposome E |
| --- | --- | --- | --- | --- | --- |
| MDA-MB-435 | 112 | 280 | 108 | 242 | 137 |
| JSQ-3 | 184 | 100 | 8 | 125 | 205 |
| DU145 | 93 | 158 | 130 | 403 | 705 |
| PANC1 | 330 | 490 | 407 | 398 | 731 |

Oligonucleotide Concentration was 2 μM
Molar Ratio of Liposomes:Oligonucleotide was 10:1

Stability of LipF(B)-AS-HER-2 In Vitro and in Blood:

As a goal of these studies was to develop a systemic delivery system for antisense oligonucleotides, it was important to determine the stability of the LipF(B)-AS-HER-2 complex in serum. Therefore, the complex was added to 50% serum and incubated at 37° C. At various times from 0–24 hours, samples were taken, the oligonucleotides labeled with $^{32}$P and percent degradation assessed by PAGE. No degradation of the AS-HER-2 oligonucleotide was found when complexed to LipF(B) for 24 hours. In contrast, over 50% of the free oligonucleotide was degraded as early as 6 hours, with virtually complete degradation by 24 hours.

The stability was also examined in mouse blood, a setting more analogous to the in vivo situation. Even after 24 hours, more than 75% of the complexed oligonucleotide remained intact. Therefore, it was concluded that the folate targeted delivery system should protect the oligonucleotide long enough in circulation to allow it to effectively reach the tumor cells.

In Vitro Chemosensitization of Cancer Cells by LipF-AS-HER-2:

The ability of the LipF(B)-delivered AS-HER-2 to sensitize MDA-MB-435, JSQ-3, DU145 and U87 (Human glioblastoma) cells to chemotherapeutic agents was evaluated. Sensitivity was determined using the XTT cell proliferation assay. Transfection with LipF(B)-AS-HER-2 substantially increased the killing effect of docetaxel upon the 435 cells. Comparison of the cells treated with LipF(B) mediated AS-HER-2, to that of cells treated with a LipF(B) control oligonucleotide (SC) indicated a greater than 30 fold increase in sensitization of 435 cells to taxotere. In contrast, only a 2.5 fold level of sensitization was evident after transfection with AS-HER-2 using the commercial Lipofectin (Life Technologies, Inc.). Treatment of JSQ-3 cells with LipF(E)-AS-HER-2 increased the effect of docetaxel almost 25 fold. Moreover, the effect of cisplatin (CDDP) on JSQ-3 cells was also increased by greater than 17 fold after treatment with AS-HER-2 complexed to transferrin-targeted Liposome A (LipT(A)). A two fold increase in sensitization of DU145 cells to docetaxel was seen after treatment with LipF(E)-AS-HER-2. Human glioblastoma cell line U87 showed a greater than 8 fold increase in chemosensitivity to the drug gemcitabine after treatment with LipF(B)-AS-HER-2.

To further demonstrate the use of the targeted liposome complex as a vector for antisense gene therapy delivery, the ability of LipF(B) carrying an anti-RAS oligonucleotide (AS-RAS, an 11 mer sequence complementary to the sequence near the initiation codon of the gene) to sensitize PANC I pancreatic carcinoma cells to docetaxel was examined. Here also a greater than 70 fold increase in drug sensitivity was induced by treatment with LipF(B)-AS-RAS. The data showed that LipF(B)-mediated antisense gene therapy can lead to a substantial increase in the effectiveness of chemotherapeutic agents in previously resistant human cancer cells.

In Vivo Studies

The ability of the LipF(B)-AS-HER-2 to target and sensitize preexisting MDA-MB-435 xenograft tumors to the chemotherapeutic agent docetaxel in vivo was examined by assessing tumor regression as well as tumor growth inhibition. Female athymic (Ncr nu/nu) mice carrying MDA-MB-435 mammary fat pad xenograft tumors of approximately 70 mm$^3$ were intravenously injected, via the tail vein, with LipF(B)-AS-HER-2 (at approximately 0.6 mM of oligonucleotides) every other day to a total of 11 injections. A total of 11 intravenous doses of docetaxel (approximately 20 mg/kg/dose every other day) were also administered to the animals. Dramatic growth inhibition of the tumors was evident in the animals receiving the combination of LipF(B)-AS-HER-2 and docetaxel. In contrast, only minimal growth inhibition was evident in those mice receiving just AS-HER-2. Moreover, while there was some docetaxel effect, these tumors began to rapidly increase in size after the cessation of treatment. Therefore, the systemically delivered, targeted liposome delivery of antisense oligonucleotides, in this case AS-HER-2, was clearly able to sensitize these tumors to the chemotherapeutic agent, strongly inhibiting tumor growth almost three weeks after the end of treatment.

EXAMPLE 22

Targeting of Adenovirus by Transferrin-Liposomes

Improving the efficiency and specificity of gene transfer remains an important goal in developing new strategies for gene therapy. Adenoviruses (Ad) are highly efficient vectors, but they are limited by lack of tumor targeting specificity and substantial immunogenicity. It has been reported that cationic lipids can form non-covalent complex with adenovirus and enhance gene transfer efficiency. But cationic lipids themselves still lack target specificity.

In this example we demonstrated that the ligand-liposome vector of the invention can also form a complex with adenovirus particles, thereby enhancing their gene transfer efficiency, and more substantially, their targeting specificity. Moreover, the use of the ligand-liposome-therapeutic molecule delivery system of the invention, when the therapeutic molecule is an intact adenovirus particle, allows efficient tumor cell targeting and systemic administration of therapeutic adenovirus for gene therapy, another novel approach to gene therapy.

Preparation of Transferrin-Liposome-Adenovirus Complex

Replication-deficient adenovirus serotype 5 containing $E.$ $coli$ β-galactosidase gene LacZ under CMV promoter, Ad5LacZ, was used in the study. The Ad5LacZ, at $1.1 \times 10^{12}$ particles (pt)/ml, or $5.5 \times 10^9$ plaque forming unit (pfu)/ml, in PBS (pH 7.4) plus 3% sucrose was used in the study. Holo-transferrin (Tf, iron-saturated, Sigma) was dissolved in water at 4–5 mg/ml and filtered with 0.22 mm filter. Tf was first diluted to 0.5 mg/ml in 10 mM HEPES buffer (pH 7.4) following which different amounts of Tf were added to 50 µl HEPES buffer in microcentrifuge tubes and mixed well. After 5–10 min incubation at room temperature, Lip (A) (DOTAP:DOPE 1:1 molar ratio) at 0.1 nmol/µl was added to the tubes so that the lipid/Tf ratios ranged from 1 nmol/1–10 g. The solutions were mixed well and incubated at room temperature for 5–10 min. $1 \times 10^6$–$1 \times 10^7$ pt adenovirus was added to each tube so that the cationic lipid/adenovirus ratios ranged from $1 \times 10^3$ to $1 \times 10^7$ lipid molecules/pt. The samples were incubated at room temperature 10–15 min and then 150 µl EMEM without serum was added to each.

In Vitro Adenoviral Transduction $5 \times 10^4$ JSQ-3 cells/well were plated in a 24-well plate. 24 hours later, the cells were washed once with EMEM without serum, 0.3 ml EMEM without serum or antibiotics was added to each well. The Ad5LacZ or Tf-Ad5LacZ complexes at different ratios in 200 µl EMEM was added to each well in duplicate. The virus to cell ratio ranged from 20 to 2000 viral particles/cell (pt/cell). After 4 hours incubation at 37° C., 5% CO2, with occasional rocking, 0.5 ml EMEM with 20% serum was added. After 2 days culture, the cells were washed once with PBS, lysed in 1X reporter lysis buffer (Promega). The cell lysates were centrifuged, transferred to a 96-well plate in duplicate, incubated with 100 µl of 150 µM 0-nitrophenyl-β-galactopyranoside in 20 mM Tris (pH 7.5) containing 1 mM $MgCl_2$ and 450 µM β-mercaptoethanol at 37° C. for 30 min. The reaction was stopped by the addition of 150 µl/well of 1 M $Na_2CO_3$. The absorbency was determined at 405 nm in an ELISA plate reader. Purified β-galactosidase (Boehringer) was used to produce a standard curve. The results were expressed as milliUnit (mU) of β-galactosidase equivalent per mg of total protein.

Histochemical Staining

For histochemical studies of LipT-Ad5LacZ transduction, 60% confluent cells in 24-well plate were transfected for 5 hours with transfection solutions as described above. After an additional 2 days in culture, the cells were fixed and stained with X-gal. Transfection efficiency was calculated as percentage of blue-stained cells.

At a viral dose of 500 pt/cell or 2.5 MOI (multiplicity of infection, or pfu/cell), 10 mU/µg protein of reporter gene product β-galactosidase was expressed by Ad5LacZ alone. The transferrin-liposome complexed virus, LipT-Ad5LacZ, at a ratio of $1 \times 10^4$ cationic lipid molecules/pt yielded a reporter gene expression of 23.5 mU/µg protein. LipT-Ad5LacZ at $1 \times 10^5$ lipid molecules/pt yielded 30.7 mU/µg expression, while LipT-Ad5LacZ at $1 \times 10^6$ molecules/pt resulted in 30.8 mU/µg expression. This represents a 2.4, 3.07 and 3.08-fold, respectively, increase in gene transduction than Ad5LacZ alone. Saturation was apparently reached at $1 \times 10^5$ lipid molecules/pt.

At a dose of 1000 pt/cell (or 5 MOI), LipT-Ad5LacZ at $10^4$ lipids/pt, demonstrated a 2.6-fold increase in reporter gene expression, while LipT-Ad5LacZ at $10^5$ lipids/pt gave 2.8-fold increase, and LipT-Ad5LacZ at $10^6$ lipids/pt, a 3.8-fold higher level of reporter gene expression than Ad5LacZ alone. Liposome complex without transferrin gave only limited enhancement. Therefore, the optimal ratios of LipT-Ad5LacZ complex appeared to be about 10–1000 cationic lipids/Tf molecule, and about $10^4$–$10^7$ cationic lipids/pt, preferably about 15–50 cationic lipids/Tf molecule and about $10^6$ cationic lipids/pt. If the lipid/pt ratio is too high, precipitation can occur.

Histochemical staining showed that Ad5LacZ alone gave 20–30% transduction efficiency while transferrin-liposome complexed adenovirus LipT-Ad5LacZ at $10^6$ lipids/pt gave 70–90% efficiency.

Other liposome compositions were tested for their ability to complex adenovirus. LipT(B) (DDAB/DOPE, 1:1 molar ratio) and LipT(D) (DOTAP/Chol, 1:1 molar ratio) showed enhanced adenoviral gene transduction into human prostate cancer cell line DU145.

The ligand-liposome delivery system of the invention was also complexed to replication-deficient adenovirus serotype 5 containing 1.7 kb of human wt p53 gene (LipT(D)-Adp53). The LipT(D)-Adp53 complex was intravenously injected into nude mice bearing DU145 prostate cancer xenograft tumors. Western analysis (performed 72 hours post injection) of the tumor demonstrated the presence of additional bands representing the exogenous human wt p53 protein present in the tumor tissue. No additional, exogenous wt p53 sequences were evident in the normal tissues (e.g. liver, lung or spleen) of the treated animal. These data show that the ligand-liposome-therapeutic molecule delivery system of the invention is capable of delivering adenovirus as the "therapeutic molecule" specifically to tumor tissue following systemic administration.

The above results demonstrated that transferrin-cationic liposomes can complex adenovirus and substantially enhance adenoviral gene transduction. The administration of ligand-liposome-adenovirus complexes represents a novel approach to human gene therapy.

EXAMPLE 23

Transferrin-Liposome-targeted Retroviral Geno Transduction

Retroviral vectors are one of the most widely used gene therapy vectors in clinical trials. As with adenoviral vectors, retroviral vectors are limited by poor tumor specificity and significant immunogenicity. In this example we demonstrate that, like adenovirus, the ligand-liposome of the invention can form a complex with retrovirus particles thereby enhancing their gene transfer efficiency, and more significantly, their targeting specificity. Moreover, the use of the ligand-liposome-therapeutic molecule delivery system of the invention, when the therapeutic molecule is an intact retrovirus particle, allows efficient tumor cell targeting and the systemic administration of retroviral vectors for gene therapy.

Replication-deficient retrovirus containing the *E. coli* LacZ gene, RvLacZ, at $1 \times 10^{10}$ particles (pt)/ml containing $3 \times 10^7$ transforming unit (TU)/ml, was employed in this study. Holo-transferrin (Tf, iron-saturated, Sigma) was dissolved in water at 4–5 mg/ml and filtered with 0.22mm filter. The LipT-RvLacZ complex was prepared similarly to that of the LipT-Ad5LacZ described above in Example 21. Briefly, Tf was first diluted to 0.5 mg/ml in 10 mM HEPES buffer (pH 7.4). Different amounts of Tf were added to 50 µl HEPES buffer microcentrifuge tubes and mixed well. After 5–10 min incubation at room temperature, cationic liposome Lip(A) (DOTAP:DOPE 1:1 molar ratio). The solutions were mixed well and incubated at room temperature for 5–10 min. $1 \times 10^6 - 1 \times 10^7$ pt retrovirus were added to each tube so that the cationic lipid/retrovirus ratios ranged from $1 \times 10^3$ to $1 \times 10^7$ lipid molecules/pt. The samples were incubated at room temperature 10–15 min and 150 µl EMEM without serum was added to each. In vitro retroviral transduction was performed as described in Example 21. The virus to cell ratio ranged from 100 to 2000 viral particles/cell (pt/cell).

At a dose of 1000 pt/cell or 3 MOI (multiplicity of infection, or TU/cell), LipT-RvLacZ at $10^5$ lipids/pt yielded a 1.5-fold increase in reporter gene expression. LipT-RvLacZ at $10^6$ lipids/pt gave a 2.3-fold increase in the level of expression as compared to RvLacZ only. The liposome complex without transferrin gave only limited enhancement. Therefore, the optimal ratios of LipT-RvLacZ complex appeared to be about 10–1000 cationic lipids/Tf molecule, and about $10^{4-10^7}$ cationic lipids/pt, preferably about 15–50 cationic lipids/Tf molecule and about $10^6$ cationic lipids/pt. If the lipid/pt ratio is too high, precipitation can occur.

Histochemical staining shows that RvLacZ alone gave 20–30% transduction efficiency while transferrin-liposome complexed retrovirus LipT-RvLacZ (106 lipids/pt) gave 60–80% efficiency.

The above results demonstrated that transferrin-cationic liposomes can complex with retrovirus and substantially enhance retroviral gene transduction.

EXAMPLE 24

Electron Microscopic Analysis of Ligand-Liposome-DNA complex

Liposomes can be observed under an electron microscope (EM), such as a transmission electron microscope (TEM) with negative staining or a scanning electron microscope (SEM). EM can reveal the structure and size distribution of the liposome complexes. EM can also be used for quality control of liposomal preparation.

In this example, we demonstrate a new, unique transferrin-liposomal structure, one that may account for the stability and efficacy observed with the ligand-liposomal-therapeutic molecule of the invention described in this application.

We observed the ligand-cationic liposomes under Transmission Electron Microscope with negative staining. A copper grid with Formvar and Carbon coating (Electron Microscopy Sciences, Fort Washington, Pa.) was used in the study. Ligand-liposome-pCMVp53 complexes were prepared as described in Examples 2 and 17. One drop of liposome complex was placed on the grid. After 5 minutes, excess liquid was removed by capillary action with filter paper at the edge of the grid. One drop of 4% Uranium Acetate was then added to the grid for negative staining. After 5 minutes, excess liquid was also removed as above. The grid was air dried at room temperature for 15 min before being put into the sample chamber of TEM. The JOEL 1200EX or JOEL 100S were used in the study according to the manufacturer's instruction. Photos were taken at magnitudes of 10–50 k, 60 kVolt. The liposome samples on the grid were prepared, freshly stained and observed within one hour.

Many publications have indicated that cationic liposome-DNA complexes have a diverse structure and size ranging from 100 nm to 1000 nm. In our study, we observed unexpectedly that the ligand-liposome-DNA complexes prepared in accordance with this invention have much smaller size and much more even size distribution. In particular, LipT(A)-p53 complexes have a size ranging from about 30–100 nm in diameter, preferably 35–65 nm (averaging about 50 nm). As the cationic liposome Lip(A) itself has a size of 15–40 nm, averaging 25 nm, when transferrin was complexed with Lip(A), the size did not change appreciably. However, thicker liposomal walls or membranes were observed, indicating that transferrin was complexed onto the liposome membrane. From the enlarged photos we observed an irregular or acentric onion-like structure in the core of the LipT(A)-DNA complex. An intermediate stage of formation of the structure, e.g., an intermediate step in the condensation of the DNA chain by LipT(A), was observed as well. When the incubation time for mixing LipT(A) with DNA was shortened from 15 to 5 minutes, more of this intermediate stage was observed.

Based upon the TEM observations, it appears that the unique structure of the LipT-DNA complex may play in important role in the high gene transfection efficiency observed in vitro and especially in vivo. The acentric onion-like core structure may be formed via the following steps during the formation of the LipT(A)-DNA complex:

Step 1. Several (4–8 or more) Tf-liposomes contact each DNA molecule, attaching to the DNA chain though electrostatic interaction.

Step 2. Each attached Tf-liposome wraps or condenses the DNA chain to form individual lamellar structures along the DNA chain.

Step 3. The lamellar structures condense to form one core lamellar structure. This solid core structure is smaller in size than the sum of 4–8 Tf-liposomes.

Step 4. During the final condensation, a phase transition from lamellar phase to an inverted hexagonal phase may occur, giving rise to the irregular or acentric onion-like structure.

The inverted hexagonal ($H_{II}$) phase is believed to be substantially more efficient than the lamellar ($L_{II}$) phase at transfection and may be related to DNA release and delivery (Koltover, I. Science 281:78.1998). Using freeze-fracture electron microscopy, Sternberg, B. (Biochim Biophys Acta 1998; 1375:23–35) described a "mappin" structure in DDAB/Chol cationic liposome-DNA complexes that had highest in vivo transfection activity. This high in vivo activity, he believed, is related to small (100–300 nm) stabilized complexes whereas high in vitro activity is associated with hexagonal lipid precipitates. No ultrastructural analysis of ligand-cationic liposome-DNA complexes is available in literature. We believe that in the presence of transferrin or other ligands, the $L_{II}$ to $H_{II}$ transition tends to occur and the formed irregular or acentric onion-like core structure is stabilized by the ligand. As for the mechanism of lamellar-to-inverted-hexagonal phase transition, besides that suggested by Koltover, the ligands may play an important role. Tf attached on liposomal surface or folate linked on the liposomal surface may help or accelerate the phase transition, giving rise to the highly efficient acentric onion-like core structures.

In the preparation conditions disclosed herein, more than 95% of LipT(A)-DNA complexes have the irregular or acentric onion-like core structure. If not for this transition, the condensed lamellar structures in Step 3–4 will preferably form regular or centered onion-like core structure to be stable. This $L_{II}$ to $H_{II}$ transition and Tf-stabilization may account for the unexpectedly high in vivo gene transfection efficiency.

Since the complexation is a four-step process, it is important, when preparing the complex, to incubate for a sufficient period of time between each mixing step, using frequent shaking, to permit the acentric onion-like core structure to form completely. For the preparation procedures disclosed herein, the incubation time should be about 5–15 minutes after each mixing and about 10–30 minutes after mixing with DNA, preferably about 15–30 minutes.

Another unique feature of the liposomes according to the invention is their evenly distributed smaller size (diameter less than about 100 nm, preferably less than about 75 nm, more preferably about 35–65 nm (50 nm average) diameter). To reach the target tumor in vivo, the liposomes must first be resistant to serum and then pass through the blood vessel (capillary) wall. The complexes of the present invention exhibit high resistance to degradation by serum. The permeable size of the capillaries in tumors is usually 50–75 nm; therefore, the complexes can pass through the capillary wall to reach the target.

The TEM structure of LipF(B)-DNA complex is similar to that of LipT(A)-DNA, and this complex has a size range of 30–100 nm, preferably 35–75 nm (average 50 nm) in diameter. The unique irregular or acentric onion-like core structures were also observed. The lamellar-to-inverted-hexagonal phase transition may occur in a similar 4-step process, which accounts for the unexpectedly high in vivo gene transfection efficiency.

EXAMPLE 25

Stability of the Ligand-cationic Liposomes

Stability is an important issue for liposomal pharmaceuticals. Liposome solutions should be stable for an extended period of time after preparation to allow for shipment and storage without substantial loss of their biological/pharmaceutical activities, to be useful as therapeutic agents. In light of the future clinical use of the ligand-liposome-therapeutic molecule complex of this invention, we examined the stability of the ligand-liposomes and the ligand-liposome-DNA complexes.

Lip(A) was prepared in water and stored under nitrogen in the dark at 4° C. for various periods of time, up to 6 months. On the day of the assay, the stored liposomes, as well as freshly prepared Lip(A), was used to make the LipT(A)-pCMVb complex. The complex was then used to transfect JSQ-3 cells using the transfection assay as described in Example 5. No appreciable difference in the level of the transgene expression was observed between the Lip(A) preparations which had been in storage for various lengths of time and the freshly prepared Lip(A). In a separate experiment, a Lip(A) preparation stored for 12 months still retained >90% of its transfection activity. The transferrin solution (5 mg/ml in water) and pCMVb plasmid DNA (0.5–1.0 μg/ml) in 10 mM Tris-HCl, 1 mM EDTA, pH 8.0) were each prepared separately. Folate-liposome complexes were found to have the same degree of stability.

The liposomes, Tf, and plasmid DNA are all individually stable in storage. But, when they are mixed together to form the LipT-DNA complex, the complex is unstable for an extended period of time. For example, the LipT-DNA complex was stable for only a few days. On day 3, only 50% transfection activity remained. For LipF-DNA, only 60% transfection activity remained after 24 hours, with virtually complete loss of activity 3 days after preparation.

Based upon these observations, it appears that the components of the ligand-liposome-therapeutic molecule complexes of this invention can advantageously be provided in kit form. The components can be mixed together sequentially, on the day of use, by first adding the Tf to the liposome, followed by the DNA solution (incubating 10–15 min. between each mixing) then adding dextrose to 5%. The complex should be administered as quickly as practical, preferably within 24 hours, following its preparation.

We claim:

1. A vector for the systemic delivery of a diagnostic or anti-tumor agent to a target cell within a host animal, comprising a complex of a cell-targeting ligand, a cationic liposome comprising a cationic lipid selected from dioleoyltrimethylammonium-propane (DOTAP) or dimethyl dioctadecylammonium bromide (DDAB) and neutral or helper lipid dioleoylphosphatidylethanolamine (DOPE), and said diagnostic or anti-tumor agent, wherein the vector has a mean diameter of less than about 100 nm and the ligand is bound directly to the liposome.

2. The vector according to claim 1 having a mean diameter of about 30 to 75 nm.

3. The vector according to claim 1 having a mean diameter of about 50 nm.

4. The vector according to claim 1 wherein said agent is a nucleic acid.

5. The vector according to claim 1 wherein said agent encodes (a) a protein or a (b) an antisense oligonucleotide.

6. The vector according to claim 1 wherein said agent is a nucleic acid encoding wild-type p53.

7. The vector according to claim 1 wherein said ligand is a tumor cell targeting ligand.

8. The vector according to claim 1 wherein said ligand is folate or transferrin.

9. The vector according to claim 1 wherein said ligand is folate.

10. The vector according to claim 1 wherein said ligand is transferrin.

11. The vector according to claim 4 wherein said liposome and said nucleic acid are present at a ratio ranging from 0.1–50 nanomoles liposome per 1.0 μg nucleic acid.

12. The vector according to claim 11 wherein said ratio ranges from 1.0–24 nanomole liposome per 1.0 μg nucleic acid.

13. The vector according to claim 11 wherein said ratio ranges from 6–16 nanomoles liposome per 1.0 μg nucleic acid.

14. The vector according to claim 1 wherein said vector has an acentric structure.

15. The vector according to claim 14 wherein said vector has a solid core.

16. A vector for delivering in vivo a therapeutically effective nucleic acid molecule to a tumor-bearing animal, the vector consisting essentially of a complex of a cell-targeting ligand selected from the group consisting of folate and transferrin, a cationic liposome comprising a cationic lipid selected from DOTAP or DDAB and neutral or helper lipid DOPE, and a nucleic acid molecule, wherein said vector has a mean diameter of less than about 100 nm and the folate or transferrin ligand is bound directly to said liposome.

17. The vector of claim 16 wherein said nucleic acid molecule encodes wild type p53.

18. The vector of claim 16 wherein said liposome and said nucleic acid molecule are in a ratio of 0.1–50 nanomole liposome per 1.0 μg nucleic acid.

19. The vector of claim 16 wherein said liposome and said nucleic acid molecule are in a ratio of 1.0–24 nanomole liposome per 1.0 μg nucleic acid.

20. The vector of claim 16 wherein said liposome and said nucleic acid molecule are in a ratio of 6–16 nanomole liposome per 1.0 μg nucleic acid.

21. The vector of claim 16 wherein said vector has an acentric structure.

22. The vector of claim 21 wherein said vector has a solid core.

23. A pharmaceutical composition comprising a vector according to claim 16 in a pharmaceutically acceptable carrier.

24. A method for systemically providing a therapeutic anti-tumor agent to an animal in need thereof, comprising systemically administering to said animal a therapeutically effective amount of a complex comprising a cell-targeting ligand, a cationic liposome comprising a cationic lipid selected from DOTAP or DDAB and neutral or helper lipid DOPE, and said therapeutic anti-tumor agent, wherein said vector has a mean diameter of less than about 100 nm and said ligand is bound directly to said liposome.

25. The method of claim 24 wherein said agent is a nucleic acid.

26. The method of claim 25 wherein said liposome and said nucleic acid are present at a ratio ranging from 0.1–50 nanomole liposome per 1.0 μg nucleic acid.

27. The method of claim 25 wherein said liposome and said nucleic acid are present at a ratio ranging from 1–24 nanomole liposome per 1.0 μg nucleic acid.

28. The method of claim 25 wherein said liposome and said nucleic acid are present at a ratio ranging from 6–16 nanomole liposome per 1.0 μg nucleic acid.

29. The method of claim 24 wherein said complex has an acentric structure.

30. The method of claim 29 wherein said complex has a solid core.

31. The method according to claim 24, wherein said vector is administered intravenously.

32. The method according to claim 24, wherein the cell-targeting ligand is folate or transferrin, and the therapeutic anti-tumor agent is a nucleic acid encoding wild-type p53.

33. The method according to claim 24 wherein the vector is administered in a pharmaceutically acceptable composition comprising a pharmaceutically acceptable vehicle.

34. A therapeutic method for the treatment or amelioration of cancer in a warm blooded animal, comprising administering to said animal a complex comprising a cancer cell targeting ligand, a cationic liposome comprising a cationic lipid selected from DOTAP or DDAB and neutral or helper lipid DOPE, and a therapeutic nucleic acid, wherein said complex has a mean diameter of less than about 100 nm and the ligand is bound directly to the liposome.

35. The method of claim 34 wherein said liposome and said nucleic acid are present at a ratio ranging from 0.1–50 nanomole liposome per 1.0 μg nucleic acid.

36. The method of claim 35 wherein said liposome and said nucleic acid are present at a ratio ranging from 1–24 nanomole liposome per 1.0 μg nucleic acid.

37. The method of claim 35 wherein said liposome and said nucleic acid are present at a ratio ranging from 6–16 nanomole liposome per 1.0 μg nucleic acid.

38. The method of claim 34 wherein said complex has an acentric structure.

39. The method of claim 38 wherein said complex has a solid core.

40. The therapeutic method according to claim 34 wherein said complex is comprised of a cell-targeting ligand selected from the group consisting of folate and transferrin, a cationic liposome and a nucleic acid encoding wild-type p53.

41. The therapeutic method according to claim 40 wherein said complex is systemically administered to a cancer-bearing warm blooded animal.

42. The therapeutic method according to claim 40, wherein said complex is intravenously administered to a cancer-bearing warm blooded animal.

43. The therapeutic method according to claim 40, wherein said complex is intratumorally administered to a cancer-bearing warm blooded animal.

44. The therapeutic method according to claim 40, further comprising administering an anti-cancer chemotherapeutic agent or an anti-cancer radiotherapy to said animal.

45. A method for preparing complexes smaller than 100 nm in diameter wherein said complexes comprise a cationic liposome comprising a cationic lipid and a neutral or helper lipid, a ligand and a nucleic acid, said method comprising the steps of:
 a) mixing said ligand with said cationic liposome to form a cationic liposome:ligand complex; and
 b) mixing said cationic liposome:ligand complex and said nucleic acid at a ratio of from 0.1–50 nanomoles liposome per 1.0 μg nucleic acid to form a cationic liposome:ligand:nucleic acid complex;
 wherein said cationic lipid comprises dioleoyltrimethylammonium-propane (DOTAP) or dimethyl dioctadecylammonium bromide (DDAB) and said neutral or helper lipid comprises dioleoylphosphatidylethanolamine (DOPE).

46. The method of claim 45 wherein said ratio is from 1–24 nanomoles liposome per 1.0 μg nucleic acid.

47. The method of claim 45 wherein said ratio is from 6–16 nanomoles liposome per 1.0 μg nucleic acid.

48. The method of claim 45 wherein said ligand is folate or transferrin.

49. The method of claim 45 wherein said liposome:ligand complex of step (a) is incubated for 5–15 minutes before performing step (b).

50. The method of claim 34, wherein said cancer comprises breast cancer, prostate cancer, head and neck cancer, ovarian cancer, pancreatic cancer, colon cancer, glioblastoma, cervical cancer, lung cancer, gastric cancer, liposarcoma, melanoma or choriocarcinoma.

51. The method of claim 34, wherein said cancer comprises breast cancer, prostate cancer, head and neck cancer, or pancreatic cancer.

52. The method of claim 51, wherein said ligand comprises transferrin or folate and said therapeutic nucleic acid encodes wt p53.

53. The method of claim 45, which further comprises combining said complex with an aqueous solution of sucrose or dextrose.

54. The vector of claim 1, wherein said cationic lipid and said neutral or helper lipid are present at a ratio of 1:(0.5–3) (molar ratio).

55. The vector of claim 10, wherein said nucleic acid, lipids and ligand are present in a ratio of 1 μg:(0.1–50 nmol):(0.1–100 μg).

56. The vector of claim 10, wherein said nucleic acid, lipids and ligand are present in a ratio of 1 μg:(5–24 nmol):(6–36 μg).

* * * * *